(12) United States Patent
Addington et al.

(10) Patent No.: US 9,846,156 B2
(45) Date of Patent: Dec. 19, 2017

(54) METHOD OF TREATMENT EMPLOYING CARDIAC GLYCOSIDE

(71) Applicant: PHOENIX BIOTECHNOLOGY, INC., San Antonio, TX (US)

(72) Inventors: Otis C. Addington, San Antonio, TX (US); Peiying Yang, Sugarland, TX (US); Robert A. Newman, Surry, ME (US)

(73) Assignee: Phoenix Biotechnology, Inc.

( * ) Notice: Subject to any disclaimer, the term of this patent is extended or adjusted under 35 U.S.C. 154(b) by 0 days.

(21) Appl. No.: 15/299,627

(22) Filed: Oct. 21, 2016

(65) Prior Publication Data

US 2017/0067897 A1   Mar. 9, 2017

Related U.S. Application Data

(60) Continuation of application No. 14/699,595, filed on Apr. 29, 2015, now Pat. No. 9,494,589, which is a
(Continued)

(51) Int. Cl.
*G01N 33/573*      (2006.01)
*C12Q 1/68*        (2006.01)
(Continued)

(52) U.S. Cl.
CPC ......... *G01N 33/573* (2013.01); *A61K 31/513* (2013.01); *A61K 31/58* (2013.01);
(Continued)

(58) Field of Classification Search
CPC .. A61K 31/513; A61K 31/58; A61K 31/7008; A61K 31/704; A61K 31/7048;
(Continued)

(56) References Cited

U.S. PATENT DOCUMENTS 4,208,479 A   6/1980   Zuk
5,872,103 A   2/1999   Belleti
(Continued)

OTHER PUBLICATIONS

Ver et al, Alterations in the properties and isoform ratios of brain Na/K-ATPase in streptozotocin diabetic rats, 1995.*
(Continued)

*Primary Examiner* — Shan Elahi
(74) *Attorney, Agent, or Firm* — Rick Matos; Innovar, L.L.C.

(57) ABSTRACT

A method of treatment employing cardiac glycoside is disclosed. A prognostic assay and kit and method of use thereof are provided. The kit and assay are used to determine the likelihood of a diseased cell or tissue having a therapeutic response to treatment with a cardiac glycoside in a disease having an etiology associated with excessive cell proliferation. The kit and assay are used to determine the ratio of isoforms of the α subunit of Na, K-ATPase obtained from the diseased cell or tissue. The kit can be used to predict the therapeutic responsiveness of cancer or tumor in a subject to treatment with a cardiac glycoside. The kit and assay can be incorporated in a method of treating a disease or disorder having an etiology associated with excessive cell proliferation with a composition comprising a cardiac glycoside.

29 Claims, 8 Drawing Sheets

Related U.S. Application Data continuation of application No. 13/754,593, filed on Jan. 30, 2013, now abandoned, which is a division of application No. 12/773,540, filed on May 4, 2010, now Pat. No. 8,367,363, which is a continuation-in-part of application No. PCT/US2008/082641, filed on Nov. 6, 2008.

(60) Provisional application No. 60/987,501, filed on Nov. 13, 2007.

(51) Int. Cl.

| | | |
|---|---|---|
| *G06F 19/12* | (2011.01) | |
| *A61K 31/58* | (2006.01) | |
| *A61K 31/704* | (2006.01) | |
| *G01N 33/574* | (2006.01) | |
| *A61K 31/7048* | (2006.01) | |
| *A61K 45/06* | (2006.01) | |
| *G01N 33/68* | (2006.01) | |
| *A61K 31/513* | (2006.01) | |
| *A61K 31/7008* | (2006.01) | |
| *A61K 36/24* | (2006.01) | |

(52) U.S. Cl.
CPC ........ *A61K 31/704* (2013.01); *A61K 31/7008* (2013.01); *A61K 31/7048* (2013.01); *A61K 36/24* (2013.01); *A61K 45/06* (2013.01); *C12Q 1/6883* (2013.01); *C12Y 306/01003* (2013.01); *G01N 33/574* (2013.01); *G01N 33/6872* (2013.01); *G06F 19/12* (2013.01); *C12Q 2600/106* (2013.01); *C12Q 2600/158* (2013.01); *G01N 2333/914* (2013.01); *G01N 2800/52* (2013.01); *G01N 2800/7023* (2013.01); *G01N 2800/7028* (2013.01)

(58) Field of Classification Search
CPC ...... A61K 36/24; A61K 45/06; C12Q 1/6883; C12Q 2600/106; C12Q 2600/158; C12Y 306/01003; G01N 2333/914; G01N 2800/52; G01N 2800/7023; G01N 2800/7028
USPC .................................................. 375/240.01
See application file for complete search history.

(56) References Cited

U.S. PATENT DOCUMENTS

| | | | |
|---|---|---|---|
| 5,891,855 A | 4/1999 | Florkiewicz | |
| 6,071,885 A | 6/2000 | Florkiewicz | |
| 6,107,283 A | 8/2000 | Florkiewicz | |
| 6,159,702 A * | 12/2000 | Traish | C07K 16/18 435/4 |
| 6,281,197 B1 | 8/2001 | Florkiewicz | |
| 6,300,311 B1 * | 10/2001 | Lee | A61K 38/1808 514/4.8 |
| 6,489,113 B1 * | 12/2002 | Traish | C07K 16/18 435/6.14 |
| 6,894,157 B2 * | 5/2005 | Sturzl | C07K 14/47 435/320.1 |
| 8,367,363 B2 | 2/2013 | Addington | |
| 2003/0018371 A1 * | 1/2003 | Chen | A61K 41/0033 607/88 |
| 2005/0123999 A1 * | 6/2005 | Valdes, Jr. | C07K 16/18 435/7.1 |
| 2005/0144660 A1 | 6/2005 | Mishra | |
| 2005/0186574 A9 * | 8/2005 | Grosse | A61K 47/48538 435/6.16 |
| 2005/0208045 A1 | 9/2005 | Vale | |
| 2006/0135441 A1 | 6/2006 | Khodadoust | |
| 2006/0205679 A1 | 9/2006 | Streeper | |
| 2007/0026092 A1 | 2/2007 | Addington | |
| 2007/0031823 A1 | 2/2007 | Bentwich | |
| 2007/0105789 A1 * | 5/2007 | Khodadoust | A61K 31/585 514/34 |
| 2007/0161591 A1 * | 7/2007 | Aronin | C12N 15/111 514/44 A |
| 2007/0212356 A1 * | 9/2007 | Chen | A61K 38/1793 424/145.1 |
| 2010/0317541 A1 | 12/2010 | Addington | |
| 2013/0324485 A1 | 12/2013 | Addington | |

OTHER PUBLICATIONS

Ver, et al., Alterations in the Properties and Isoform Ratios of Brain Na+/K+-ATPase in Streptozotocin Diabetic Rats. Biochemica et Biophysica Acta. Jul. 26, 1995, vol. 1237, No. 2, pp. 143-150.

Mijatovic, T. et al. "The alpha/ subunit of 15-20 the sodium pump could represent a novel target to combat non-small cell lung cancers." The Journal of Pathology. Jun. 2007 LNKD-PUBMED:17471453, vol. 212, No. 2, Jun. 2007 (Jun. 6, 2007) pp. 170-179, xp002607332. ISSN:0022-3417.

Yang, Peiying et al. "Oleandrin-mediated inhibition of human tumor cell proliferation: Importance of Na, K-ATPase alpha subunits as drug targets" Proceedings of the American Association for Cancer Research Annual Meeting, vol. 49, Apr. 2008 (Apr. 2008), p. 359, XP8128306.

Newman, Robert A et al. "Cardiac glycosides as novel cancer therapeutic agents." Molecular Interventions, Feb. 2008 (Feb. 2008), pp. 36-49, XP002607334. ISSN: 1534-0384.

Mijatovic et al., Cardiotonic steroids on the road to anti-cancer therapy; Biochim. Biophys. Acta (2007), 1776, 32-57.

Blanco, G. et al. "Isozymes of the Na, K-ATPase: heterogeneity in structure, diversity in function".Am. J.Physiol. 275 (Renal Physiol. 44): F633-F650, 1998.

Rajasekaran, S.A. et al. "Reduced Expression of Beta Subunit of Na/K-ATPase in Human Clear Cell Renal Cell Carcinoma." J. Urol.162:574-580,1999.

Avila, J. et al. "Opposite expression pattern of the human Na/K-ATPase Beta-1 Isoform in Stomach and Colon Adenocarcinomas." Ann. N.Y. Acad. Sci. 834: 633-635, 1997.

Espineda, C. et al. "Analysis of the Na, K-ATPase alpha and beta expression profiles of Bladder Cancer Using Tissue Microarrays". Cancer 97: 1859-1868, 2003.

Jung, M. et al. "Identification of Differentially Expressed Genes in Normal and Tumor Human Gastric Tissue". Genomics 69: 281-286, 2000.

Sakai et al. "Up-regulation of Na+, K+-APTase alpha-3 isoform and down-regulation of alpha-1 isoform in human colorectal cancer". (FEBS Letters 563: 151-154, 2004).

Yang, Peiying et al. "Oleandrin-mediated inhibition of human tumor cell proliferation: Importance of Na, K-ATPase alpha subunits as drug targets" in Molecular Cancer Therapeutics (2009), 8(8), 2319-2322.

Harlow Antibodies, a laboratory manual. (Cold Spring Harbor, New York; Cold Spring Harbor Laboratory Press, 1989, p. 141-155).

\* cited by examiner

FIG. 6A
FIG. 6B
FIG. 6C
FIG. 6D
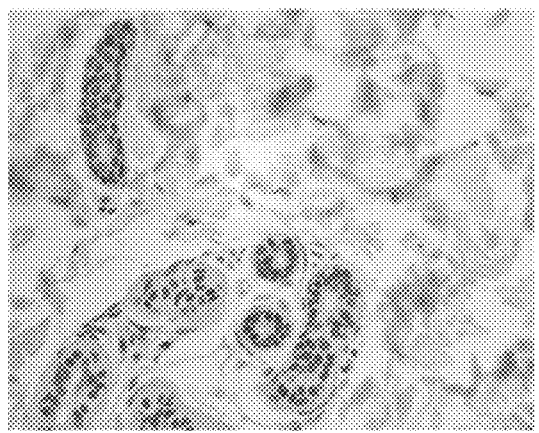
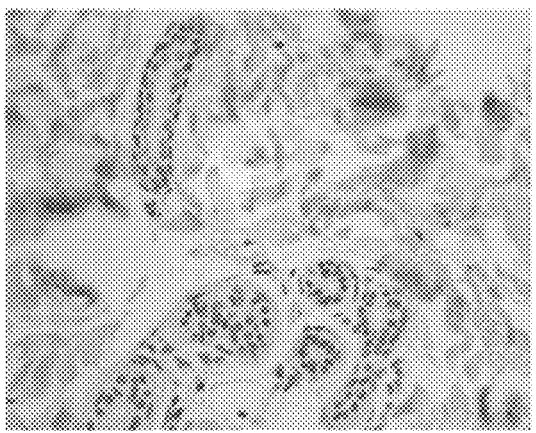
FIG. 6E
FIG. 6F FIG. 7A
FIG. 7B
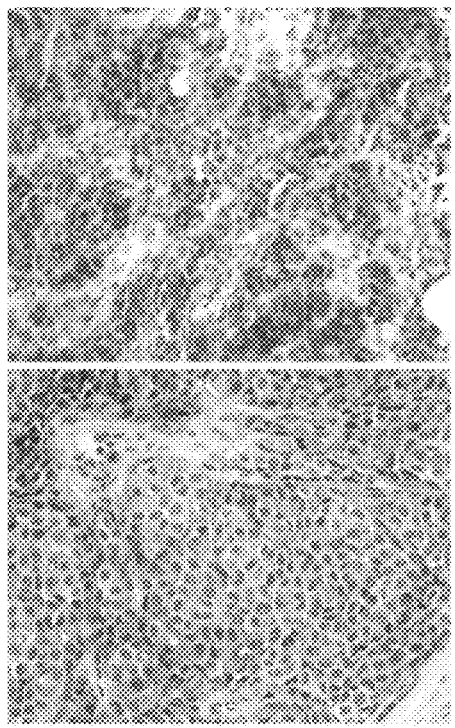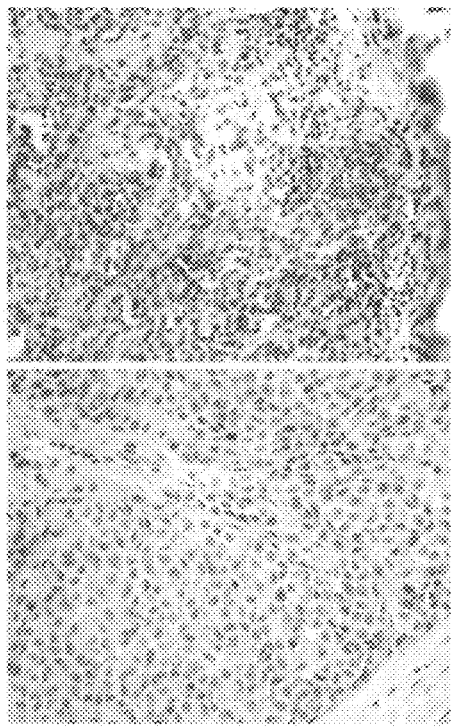
FIG. 7C
FIG. 7D
FIG. 7E
FIG. 7F
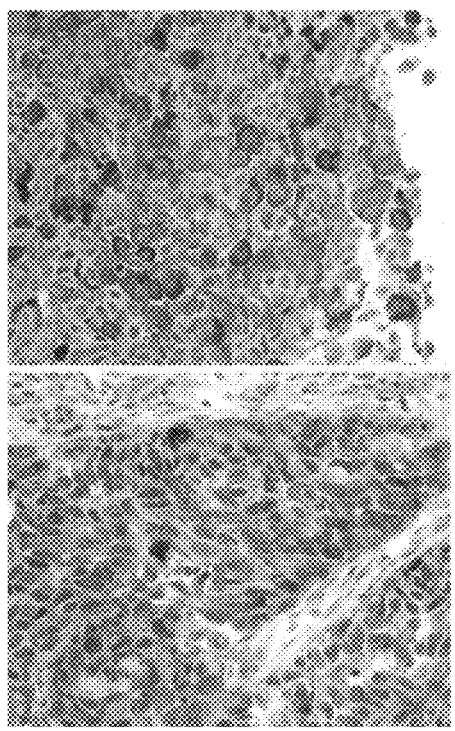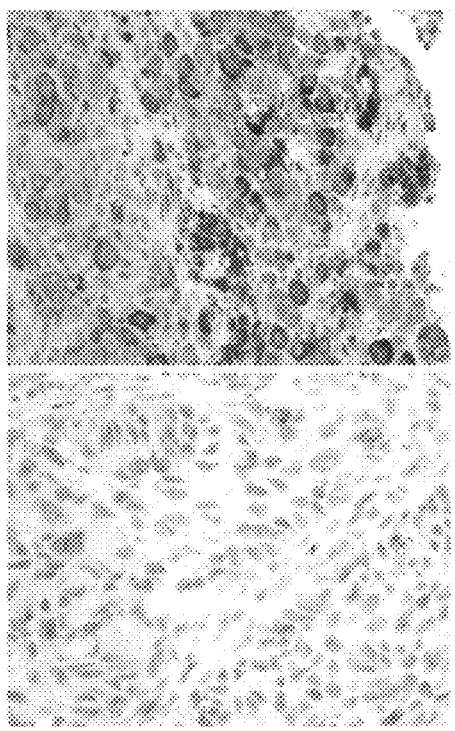
FIG. 7G
FIG. 7H

METHOD OF TREATMENT EMPLOYING CARDIAC GLYCOSIDE

CROSS-REFERENCE TO EARLIER FILED APPLICATIONS

The present application is continuation of and claims the benefit of U.S. application Ser. No. 14/699,595 filed Apr. 29, 2015, which is a continuation of and claims the benefit of application Ser. No. 13/754,593 filed Jan. 30, 2013, which is a division of and claims the benefit of U.S. application Ser. No. 12/773,540 filed May 4, 2010, now U.S. Pat. No. 8,367,363 issued Feb. 5, 2013, which is a continuation-in-part of and claims the benefit of PCT Application No. PCT/US2008/082641, filed Nov. 6, 2008, which claims the benefit of U.S. Provisional Application No. 60/987,501, filed Nov. 13, 2007, the entire disclosures of which are hereby incorporated by reference.

FIELD OF THE INVENTION

The present invention concerns a method of determining the prognosis in cancer chemotherapy with a cardiac glycoside. In particular, the invention concerns a method for determining the probability of whether or not an in vitro or in vivo cell disease or disorder having an etiology associated with excessive cell proliferation will be therapeutically responsive to treatment with a cardiac glycoside.

BACKGROUND OF THE INVENTION

Many diseases and disorders having an etiology associated with excessive cell proliferation are fatal. The most common of these are cancer and tumors. Noncancerous proliferative diseases can also be life-threatening, however, or lead to a diminished quality of life. These may include, for example: 1) autoimmune diseases such as antigen-induced arthritis and allergic encephalomyelitis, 2) chronic inflammatory proliferative diseases such as rheumatoid arthritis, systemic-onset juvenile chronic arthritis, osteoporosis, and psoriasis, 3) proliferative diseases of the breast including fibrocystic disease, 4) proliferative diseases of the prostate including benign prostatic hyperplasia (BPH), 5) proliferative diseases of the eye including proliferative diabetic retinopathy, and 6) vascular proliferative diseases including atherosclerosis and coronary stenosis. Many efforts have been made to develop curative or ameliorative therapies for these diseases and disorders; however, no comprehensive or universally curative therapy has been developed, even though there are numerous chemotherapeutic approaches that have been proven to be effective against various different cancers, tumors and other types of proliferative disease.

Chemotherapeutic agents are prescribed individually or in combination by clinicians in attempts to develop regimens that are tailored to individual patients' needs. Even so, a key hurdle toward the development of these tailored regimens is the unpredictability of the efficacy of chemotherapeutic agents against specific cancer or tumor phenotypes. Clinicians are forced to deal with these deadly diseases by using hit or miss approaches. They must rely upon a historic review of the recognized or indicated uses of particular chemotherapeutic agents and then speculate or guess as to whether or not a particular single chemotherapeutic agent or combination of chemotherapeutic agents will be therapeutically effective against the cancer or tumor the clinician is attempting to cure. Such a conventional has limited success in the clinic.

Clinicians are in need of a prognostic assay that can predict with some reasonable level of certainty whether or not a particular cancer or tumor phenotype will be therapeutically responsive to a particular single chemotherapeutic agent or combination of therapeutic agents. This type of prognostic assay is extremely useful for chemotherapeutic agents that have a limited use history, such as those that are just entering the clinical environment. It would be extremely beneficial to clinicians to have such a prognostic assay for one or more of such chemotherapeutic agents.

Preclinical studies and retrospective examination of patient data have suggested the potential value of cardiac glycosides, (e.g. bufalin, digoxin, digitoxin, ouabain and oleandrin), in the treatment of various cancers including breast, lung, prostate and leukemia, for example.

One of the pharmacological mechanisms of action of cardiac glycosides involves their ability to bind to the ion exchange pump, Na, K-ATPase and to inhibit the activity of this particular enzyme. Na, K-ATPase, the transmembrane protein that catalyzes the active transport of $Na^+$ and $K^+$ across the plasma membrane, is a well established pharmacologic receptor for cardiac glycosides. This enzyme hydrolyzes ATP and uses the free energy to drive transport of $K^+$ into the cell and $Na^+$ out of cells, against their electrochemical gradients (Hauptman, P. J., Garg, R., and Kelly, R. A. Cardiac glycosides in the next millieum. Prog. Cardiovasc. Dis. 41: 247-254, 1999).

Na, K-ATPase is composed of two heterodimer subunits, the catalytic α-subunit and the glycosylated β-subunit. There is also a γ subunit, but it has not been studied in detail. The α-subunit has binding sites for ATP, $Na^+$, $K^+$, and cardiac glycosides. The β-subunit functions to stabilize the catalytic α-subunit and may play a regulatory role as well. Four different α isoforms (α1, α2, α3, α4) and three different β isoforms (β1, β2, and β3) have been identified in mammalian cells. The relative expression of each type is markedly altered in normal and diseased states. The expression of α isoforms is tissue-type specific and varies among rodent and human tissues (Blanco, G. and Mercer, R. W. Isozymes of the Na, K-ATPase: heterogeneity in structure, diversity in function. Am. J. Physiol. 275 (Renal Physiol. 44): F633-F650, 1998). An altered expression of Na, K-ATPase isoforms in human cancers such as renal, lung, hepatocellular, and colon has also been reported in contrast to those in corresponding normal tissues (Rajasekaran, S. A., Ball, W. J., Bander, N. H., Pardee, J. D. and Raj asekaran, A. K. Reduced expression of beta subunit of Na/K-APTase in human clear cell renal cell carcinoma. J. Urol. 162: 574-580, 1999; Avila, J., Lecuona, E., Morales, M., Soriano, A., Alonso, T., and Martin-Vasallo, P. Opposite expression pattern of the human Na/K-ATPase beta-1 isoform in stomach and colon adenocarcinomas. Ann. N.Y. Acad. Sci. 834: 633-635, 1997; Espineda, C., Seligson, D. B., Ball, W. J., Rao, J., Palotie, A., Horvath, S., Huang, Y., Shi. T and Rajasekaran, A. K. Analysis of the Na, K-ATPase α- and β-subunit expression profiles of bladder cancer using tissue microarrays. Cancer 97: 1851868, 2003; Jung, M. H., Kim, S. C., Jeon, G. A., Kim, S. H., Kim, Y., Choi, K. S., Park, S. I., Joe, M. K., and Kimm, K. Identification of differentially expressed genes in normal and tumor human gastric tissue. Genomics 69: 281-286, 2000). Additionally, the apparent affinity of cardiac glycosides to the different α isoforms is quite different. Binding of cardiac glycosides to the α1 isoform is less than that which occurs with the α2 and α3 isoforms which are 250-fold or higher more sensitive to inhibition by this type of drug (Blanco, G. and Mercer, R. W. Isozymes of the Na, K-ATPase: heterogeneity in structure, diversity in function. Am. J. Physiol. 275 (Renal Physiol. 44): F633-F650, 1998). Sakai et al. (FEBS Letters 563: 151-154, 2004) report that expression of the α3 subunit isoform is increased in human colorectal cancer cells as compared to normal colorectal cells.

Oleandrin and oleandrigenin inhibit proliferation of human prostate cancer cells through induction of apoptosis which is due, at least in part, to an increase in intracellular $Ca^{2+}$ via inhibition of Na, K-ATPase (McConkey, D. J., Lin, Y., Nutt, L. K., Ozel, H. Z., and Newman, R. A. Cardiac glycosides stimulate $Ca^{2+}$ increases and apoptosis in androgen-independent, metastatic human prostate adenocarcinoma cells. Cancer Res. 60: 3807-3812, 2000). Oleandrin and oleandrigenin also inhibit export of fibroblast growth factor-2 through membrane interaction and inhibition of Na, K-ATPase activity (Smith, J. A., Madden, T., Vijjeswarapu, M., and Newman, R. A. Inhibition of export of fibroblast growth factor-2 (EGF-1) from the prostate cancer cell lines PC3 and DU145 by Anvirzel and its cardiac glycoside component, oleandrin. Biochem. Pharmacol. 62: 469-472, 2001).

While Na, K-ATPAase subunit α1 is present in many tissues because the $α_1β_1$ complex is considered as 'housekeeping' genes, α3 is predominantly detected in excitable tissues, renal cortex, medulla, and papilla as well as nervous tissues Nerium oleander is an ornamental plant widely distributed in subtropical Asia, the southwestern United States, and the Mediterranean. Its medical and toxicological properties have long been recognized. It has been used, for example, in the treatment of hemorrhoids, ulcers, leprosy, snake bites, and even in the induction of abortion. Oleandrin, an important component of oleander extract, is a potent inhibitor of human tumor cell growth (Afaq F et al. *Toxicol. Appl. Pharmacol.* 195:361-369, 2004). Oleandrin-mediated cell death is associated with calcium influx, release of cytochrome C from mitochondria, proteolytic processes of caspases 8 and 3, poly(ADP-ribose) polymerase cleavage, and DNA fragmentation.

It has been demonstrated that oleandrin is the principal cytotoxic component of *Nerium oleander* (Newman, et al., *J. Herbal Pharmacotherapy*, vol. 13, pp. 1-15, 2001). Oleandrin is a cardiac glycoside that is exogenous and not normally present in the body. Oleandrin induces apoptosis in human but not in murine tumor cell lines (Pathak et al., *Anti-Cancer Drugs*, vol. 11, pp. 455-463, 2000), inhibits activation of NF-κB (Manna et al., Cancer Res., vol. 60, pp. 3838-3847, 2000), and mediates cell death in part through a calcium-mediated release of cytochrome C (McConkey et al., *Cancer Res.*, vol. 60, pp. 3807-3812, 2000). A Phase I trial of a hot water oleander extract (i.e. Anvirzel™) has been completed recently (Mekhail et al., *Am. Soc. Clin. Oncol.*, vol. 20, p. 82b, 2001). It was concluded that oleander extracts can be safely administered at doses up to 1.2 ml/m²/d. No dose limiting toxicities were found.

Ouabain, a cardiac glycoside endogenous to the body, was reported to enhance in vitro radiosensitivity of A549 human lung adenocarcinoma cells but was ineffective in modifying the radioresponse of normal human lung fibroblasts (Lawrence, *Int. J. Radiat. Oncol. Biol. Phys.*, vol. 15, pp. 953-958, 1988). Ouabain was subsequently shown to radiosensitize human tumor cells of different histology types including squamous cell carcinoma and melanoma (Verheye-Dua et al., *Strahlenther. Onkol.*, vol. 176, pp. 186-191, 2000). The cardiac glycoside oleandrin also has the ability to enhance the sensitivity of cells to the cytotoxic action of ionizing radiation (U.S. patent application Ser. No. 10/957, 875 to Newman, et al. and Nasu et al., Cancer Lett. Vol 185, pp. 145-151, 2002). U.S. Pregrant Patent Application Publication No. 20050112059 to Newman et al. discloses the enhancement of radiotherapy in the treatment of cancer by administration of oleandrin.

Chen et al. (*Breast Cancer Research and Treatment* (2006), 96, 1-15) suggest that cardiac glycosides, such as ouabain and digitalis, might be useful toward developing anti-breast cancer drugs as both $Na^+$, $K^+$-ATPase inhibitors and ER antagonists.

Smith et al. (*Biochemical Pharmacology* (2000), 62, 1-4) report that ANVIRZEL, and its key cardiac glycoside component oleandrin, inhibits the exportation of a tumor growth factor, fibroblast growth factor-2 (FGF-2), from the prostate cancer cell lines PC3 and DU145.

Newman et al. (*J. Experimental Therapeutics and Oncology* (2006), 5, 167-181) report that incubation of human malignant melanoma BRO cells with oleandrin results in a time-dependent formation of reactive oxygen species, superoxide anion radicals, that mediate mitochondrial injury, loss of cellular glutathione (GSH) pools and, ultimately, tumor cell death.

Extraction of glycosides from plants of *Nerium* species has provided pharmacologically/therapeutically active ingredients from *Nerium oleander*. Among these are oleandrin, nerine, and other cardiac glycoside compounds. The plant extracts are useful in the treatment of cell-proliferative diseases in animals. Oleandrin extracts obtained by hot-water extraction of *Nerium oleander*, sold under the trademark ANVIRZEL™, are commercially available and contain the concentrated form or powdered form of a hot-water extract of *Nerium oleander*.

Huachansu is an extract obtained from toad skin and it comprises bufadienolides, such as bufalin, a cardiac glycoside. HuaChanSu is an approved medication for the treatment of cancer in China. It has been used to treat various cancers, including hepatic, gastric, lung, skin, and esophageal cancers.

In view of the important utility of cardiac glycosides in treating diseases or disorders having an etiology associated with cell proliferation, a need remains for a method of predicting the therapeutic response of the disease or disorder to a cardiac glycoside. No such method is disclosed in or suggested by the prior art.

SUMMARY OF THE INVENTION

The invention provides a method of predicting the efficacy of a cardiac glycoside or of a composition containing a cardiac glycoside against a particular phenotype of a disease or disorder having an etiology associated with excessive cell proliferation. The inventors have discovered that the sensitivity or therapeutic responsiveness of such a disease or disorder to treatment with a cardiac glycoside is dependent upon the ratio of α3 isoform to α1 isoform expression of Na, K-ATPase subunits in cells or tissues having the disease or proliferative disorder. In general, the higher the ratio of α3 isoform to α1 isoform expression of Na, K-ATPase in cells or tissues, the more sensitive (therapeutically responsive) those cells are to cardiac glycosides. That is, the higher the α3 isoform (drug sensitive) to α1 (drug insensitive) isoform ratio, the more sensitive that cell or tissue will be to inhibition of proliferation by cardiac glycosides.

One aspect of the invention provides an in vitro prognostic assay useful for predicting the in vivo therapeutic responsiveness of a disease or disorder, having an etiology associated with excessive cell proliferation, to treatment with a cardiac glycoside or composition comprising a cardiac glycoside, the assay comprising:

determining the ratio of α3 isoform to α1 isoform of the Na, K-ATPase α-subunit in a sample obtained directly or indirectly from diseased in vivo cellular tissue of a subject with a disease or disorder having an etiology associated with excessive cell proliferation, the sample comprising one or more isoforms of the α subunit of Na, K-ATPase; and determining the probability of a therapeutic response in the subject were the subject to be treated with a therapeutically relevant dose of cardiac glycoside according to a prescribed dosing regimen.

In some embodiments: 1) the assay further comprises predicting that the cellular tissue will be therapeutically responsive to treatment with a cardiac glycoside if the ratio is greater than or equal to at least 1; 2) the assay further comprises predicting that the cellular tissue will be at least partially therapeutically responsive to treatment with a cardiac glycoside if the ratio is within the range of 0.5 to 1.0; 3) the assay further comprises predicting that the cellular tissue will be substantially therapeutically non-responsive to treatment with a cardiac glycoside if the ratio is less than 0.3; 4) the assay also further comprises predicting that those tissues having α subunit ratio within the range of 1 to 100 will be more therapeutically responsive than those having an isoform ratio less than 1; 5) the assay further comprises predicting that those tissues with only detectable α3 isoform and no detectable α1 isoform will be the most therapeutically responsive to cardiac glycosides; and/or 6) the assay further comprises predicting that the cellular tissue will be therapeutically responsive to treatment with a cardiac glycoside if the ratio is ≥2, ≥3, ≥4, ≥5, ≥7, ≥9, ≥10, ≥15, ≥20, ≥25, ≥40, ≥50, ≥75 or ≥100.

In some embodiments, the probability that there will be a therapeutic response is related to the ratio of α3 isoform to α1 isoform of Na, K-ATPase according to the following table:

| Ratio | Probability that there will be a therapeutic response in the subject |
|---|---|
| 0.3 to less than 0.5 | 20 to <30% |
| 0.5 to less than 1 | 30 to 50% |
| >/=1 | >50% |
| >10 | >75% |

In the table above, the therapeutic response can be a partial or full therapeutic response or delayed time to progression.

In some embodiments: 1) the step of determining comprises quantifying the level of expression of each the α3 subunit isoform of Na, K-ATPase and the α1 subunit isoform of Na, K-ATPase in the in vitro sample or biopsy sample, and calculating the ratio thereof; 2) the step of determining comprises determining the amount of the α3 subunit isoform of Na, K-ATPase relative to amount of the α1 subunit isoform of Na, K-ATPase in the in vitro sample, and calculating the ratio thereof; 3) the assay further comprises conducting a statistical analysis on data from which the ratio is determined; 4) the sample is cellular tissue, cellular mass, cellular lysate, membrane preparations prepared from these, or fixed histopathology slides thereof; 5) the sample is an in vitro sample; 6) the sample comprises at least two isoforms of the α subunit of Na, K-ATPase; 7) the sample comprises at least the α1 and α3 isoforms of the α subunit of Na, K-ATPase; 8) the method further comprises lysing or disrupting cells or tissues or biopsy samples or fixing tissue sections for histopathologic examination from diseased in vivo cellular tissue to form the sample; 9) the method comprises performing a Western blot assay or immunohistochemical staining assay on the sample to determine the amount and relative expression of α3 subunit isoform of Na, K-ATPase relative to the α1 subunit isoform of Na, K-ATPase in the sample, and calculating the ratio thereof; 10) the method further comprises conducting a radiometric or densitometric analysis of a gel in order to determine the content of α3 subunit isoform of Na, K-ATPase relative to the content of α1 subunit isoform of Na, K-ATPase in the sample; 11) the method further comprises conducting a radiometric or densitometric analysis of a gel in order to detect the presence of and quantify the content of α3 subunit isoform of Na, K-ATPase and of α1 subunit isoform of Na, K-ATPase in the sample; 12) comparing the content of α3 subunit isoform of Na, K-ATPase and of α1 subunit isoform of Na, K-ATPase in the sample relative to the content of α3 subunit isoform of Na, K-ATPase and/or of α1 subunit isoform of Na, K-ATPase in a positive control sample and/or a negative control sample; and/or 13) comparing the content of α3 subunit isoform of Na, K-ATPase and of α1 subunit isoform of Na, K-ATPase in a tissue sample where expression of only one of the α3 and α1 subunit isoforms is known to occur as a control.

In some embodiments: 1) the diseased cellular tissue is obtained from a subject such as a mammal; 2) the diseased cellular tissue is obtained from a human, cow, dog, cat, horse, pig or other domesticated animals whether of commercial value or not; 3) the disease or disorder having an etiology associated with excessive cell proliferation is cancer or tumor or other proliferative diseases that impact adversely on human or animal quality of life; and/or 4) the cancer or tumor is selected from the group consisting of colorectal cancer, head and neck cancer, adrenal cortical cancer, anal cancer, bile duct cancer, bladder cancer, bone cancer, bone metastasis, sarcomas of bone, brain cancer, breast cancer, cervical cancer, non-Hodgkin's lymphoma, rectal cancer, esophageal cancer, eye cancer, gallbladder cancer, gastrointestinal carcinoid tumor, gestational trophoblastic disease, Hodgkin's disease, Kaposi's sarcoma, kidney cancer, laryngeal and hypopharyngeal cancer, liver cancer, lung cancer (both non small cell and small cell carcinomas), lung carcinoid tumors, malignant mesothelioma, metastatic cancer, multiple myeloma, myelodysplastic syndrome, nasal cavity and paranasal cancer, nasopharyngeal cancer, neuroblastoma, neoplasms of the central nervous system, oral cavity and oropharyngeal cancer, osteosarcoma, ovarian cancer, pancreatic cancer, penile cancer, pituitary cancer, prostate cancer, retinoblastoma, salivary gland cancer, sarcoma, skin cancer, stomach cancer, testicular cancer, thymus cancer, thyroid cancer, cancer of the ureter; uterine sarcoma, vaginal cancer, vulva cancer or Wilm's tumor.

In some embodiments: 1) the method further comprises identifying a subject having a disease or disorder having an etiology associated with excessive cell proliferation; 2) the method further comprises the step of obtaining a sample of diseased cells from the subject; 3) the method comprises providing information specifying how to perform analyses for the α3 and α1 isoforms of the α subunit of Na,K-ATPase; and/or 4) the method comprises providing information detailing how to interpret prognostic data.

In some embodiments, proliferative diseases include but are not limited to: 1) autoimmune diseases such as antigen-induced arthritis and allergic encephalomyelitis; 2) chronic inflammatory proliferative diseases such as rheumatoid arthritis, systemic-onset juvenile chronic arthritis, osteoporosis, and psoriasis; 3) proliferative diseases of the breast including fibrocystic disease; 4) proliferative diseases of the prostate including benign prostatic hyperplasia (BPH); 5) proliferative diseases of the eye including proliferative diabetic retinopathy; and 6) vascular proliferative diseases including atherosclerosis and coronary stenosis. In some embodiments, two or more proliferative diseases are being treated simultaneously.

Cancers believed to be particularly responsive to treatment with cardiac glycosides, based on laboratory research with human tumor cell lines, include prostate cancer, lung cancer, breast cancer, bladder cancer, osteogenic sarcoma, brain cancer (glioblastoma multiforma) and colon cancer. The cancers can be of human, non-human or animal origin.

In some embodiments: 1) the cardiac glycoside is selected from the group consisting of oleandrin, ouabain, bufalin, digitoxin, digoxin, cinobufatalin, cinobufagin, and resibufogenin; 2) the cardiac glycoside is present in pure form whether derived through extraction of a plant or animal source, synthesized or manufactured through chemical modification (e.g. derivatization) of an available cardiac glycoside; 3) the cardiac glycoside is present in an extract; 4) the cardiac glycoside is present in a pharmaceutical formulation or composition; 5) the cardiac glycoside has been obtained from an oleander plant mass; 6) the oleander plant mass comprises *Nerium* species, such as *Nerium oleander*, or of *Thevetia* species, such as *Thevetia nerifolia* (otherwise known as yellow oleander); and/or 7) the cardiac glycoside extract was prepared by supercritical fluid (SCF) extraction optionally in the presence of a modifier.

In some embodiments: 1) the SCF extract further comprises at least one other pharmacologically active agent aside from the cardiac glycoside; 2) the other active agent may contribute to the therapeutic efficacy of the cardiac glycoside when the extract is administered to a subject; 3) the other active agent functions additively or synergistically to contribute to the therapeutic efficacy of the cardiac glycoside; and/or 4) the extract has been obtained from toad skin or secretions derived therefrom.

Another aspect of the invention provides a kit suitable for use in conducting the prognostic assay of the invention. The kit comprises: a) a first primary antibody having a binding affinity for the $\alpha 3$ subunit isoform of Na, K-ATPase; and b) a second primary antibody having a binding affinity for the $\alpha 1$ subunit isoform of Na, K-ATPase. The kit can be adapted for use in conducting a Western blot gel electrophoretic assay and/or for conducting an immunohistochemical staining assay.

The kit optionally further comprises: a) a lysis composition; b) a positive control sample comprising $\alpha 3$ subunit isoform of Na, K-ATPase; c) a positive control sample comprising $\alpha 3$ subunit isoform of Na, K-ATPase and $\alpha 1$ subunit isoform of Na, K-ATPase; d) a negative control sample comprising a 1 subunit isoform of Na, K-ATPase and excluding $\alpha 3$ subunit isoform of Na, K-ATPase; e) a secondary antibody, a goat anti-mouse IgG-HRP (which may be used for example for visualization of proteins of interest); f) gel-forming material suitable for gel electrophoretic analysis; g) radiolabeled or colored (chromic, capable of generating a visually or instrumentally detectable signal) molecular weight markers; h) instructions for use of kit and performance of the prognostic assay; i) densitometer or radiometer; j) aqueous liquid medium; k) gel/membrane preparation kit; l) blocking solution; m) wash buffer; n) materials comprising a Western blot analysis kit; or o) a combination thereof.

In some embodiments of the kit: a) the first primary antibody has specific binding affinity for the $\alpha 3$ subunit isoform of Na, K-ATPase; b) the second primary antibody has specific binding affinity for the $\alpha 1$ subunit isoform of Na, K-ATPase; c) the secondary antibody is Goat $\alpha$ mouse IgG horse radish peroxidase or comprises other secondary antibodies from species other than mouse raised against mouse IgG with an appropriate marker attached such as horse radish peroxidase; and/or d) the primary antibodies are monoclonal antibodies.

In some embodiments, the immunohistochemical staining assay kit comprises: a) antigen unmasking solution (which can be high pH or citric acid based); b) buffer; c) endogenous-peroxide activity-quenching material (which can comprise hydrogen peroxide, optionally in methanol); d) anti-Na,K-ATPase $\alpha 3$ subunit isoform antibody and/or anti-Na,K-ATPase $\alpha 1$ subunit isoform antibody; e) non-immune mouse IgG1 antibody; f) universal antibody reagent comprising a mixture of anti-rabbit IgG and anti-mouse IgG reagents; g) primary chemical stain, such as diaminobenzidine; h) a general counter-chemical stain, such as haematoxylin or eosin; i) specific cellular organelle stain, such as that used for staining nuclei (e.g. ethidium bromide, bisbenzimidazol or potassium aluminum sulphate) or mitochondria (e.g. Mito tracker red, 10-nonyl acridine orange); j) materials comprising an immunohistochemical staining kit; or k) a combination of two or more thereof. Using adjacent sections of tissues or cells, staining of $\alpha 1$ subunit isoform can be done in a manner similar to that used for the staining of $\alpha 3$ subunit isoform in which the appropriate specific primary antibodies to $\alpha 1$ subunit isoform and $\alpha 3$ subunit isoform are used. As used herein, a specific cellular organelle stain is an agent or combination of agents used to specifically stain a particular type of organelle (mitochondrion, nucleus, nucleolus, golgi apparatus, vacuole, etc.) in a cell (human, non-human, or animal).

In some embodiments, the immunohistochemical staining assay comprises the steps of: a) providing a sample of mammalian tissue; b) immunochemically staining the $\alpha 3$ isoform and $\alpha 1$ isoforms of the $\alpha$-subunit of Na, K-ATPase present in the sample; c) determining the content of $\alpha 3$ subunit isoform of Na, K-ATPase and the content of $\alpha 1$ subunit isoform of Na, K-ATPase in the sample; and d) determining the ratio of $\alpha 3$ isoform to $\alpha 1$ isoform present in the sample.

In some embodiments, the immunohistochemical staining assay comprises the steps of: a) providing a sample of mammalian tissue; b) performing an antigen retrieval procedure on the tissue; c) quenching endogenous peroxide activity in the tissue; d) exposing the quenched tissue to anti-Na,K-ATPase $\alpha 3$ subunit isoform and/or anti-Na,K-ATPase $\alpha 1$ subunit isoform primary antibodies; e) exposing the antibody-treated tissue to secondary anti-rabbit IgG, anti-mouse IgG antibodies or a combination thereof; f) exposing the IgG-treated tissue to primary stain; g) exposing the stained tissue to counter-stain to form an immunohistochemically-stained tissue; h) analyzing the immunohistochemically-stained tissue by visual or photometric means; and i) quantifying the amount of $\alpha 3$ and/or $\alpha 1$ isoforms present in the mammalian tissue Quantitation of the isoform antibody staining can be done, for example, if the secondary antibody is biotinylated. Then a Vectastatin ABC stain can be added and incubated for 30 min. Following washes of the stained sections, they are then incubated with diaminobenzidine substrate to develop a suitable level of staining. The quantitation of the stained tissues can then be performed manually by grading the intensity of the stain or electronically using computerized image capture and digital scanning of fields of interest. Quantitation can be further facilitated using digital image software that is commercially available. In some embodiments, the assay further comprises the step of: j) washing the tissue resulting from step a); k) washing the tissue resulting from step c); l) providing negative control sections (those not having tumor or cancer) as a "no primary" control; m) exposing the negative control sections with a non-immune mouse IgG1 antibody; n) washing the tissue resulting from step e); o) washing the tissue resulting from step f); and/or washing the tissue resulting from step g). The washing can be conducted with water, buffered water, and/or TBS (about 50 mM Tris HCl, about 300 mM NaCl, about 0.1% Tween 20, pH about 7.6).

The positive control sample can be tissue, cellular mass, cellular lysate or membrane preparations prepared from these which can be obtained through biopsy or other means of surgical excision. The negative control sample can be tissue, cellular mass, or cellular lysate or membrane preparations prepared from these that are known through prior analyses not to contain α3 isoform of the α-subunit of Na, K-ATPase. In some embodiments, the negative control consists of a cellular mass of rodent (mouse or rat) tumor tissue or mouse or rat cells grown in vitro.

Analytical methods that are alternative means of determining relative Na, K-ATPase α subunit isoform composition and ratios can be employed according to the invention to determine the α3 to α1 isoform ratio. These might consist, for example, of use of appropriate antibodies in an ELISA (enzyme linked immunoabsorbant assay) or protein tissue or cell lysate array. Alternatively, it is possible to use Northern blot analyses and related techniques (e.g. rtPCR, real time polymerase chain reaction) for measurement of mRNA to different Na, K-ATPase α-subunit isoforms. An immunohistochemical staining assay can also be used to quantify the amounts of α3 isoform and α1 isoform of the α-subunit present in a sample.

Another aspect of the invention provides a method of treating, in a subject, a disease or disorder having an etiology associated with excessive cell proliferation with a composition comprising cardiac glycoside, the method comprising:
determining the ratio of α3 isoform to α1 isoform of the α subunits of Na, K-ATPase in a sample obtained directly or indirectly from diseased in vivo cellular tissue of the subject with a disease or disorder having an etiology associated with excessive cell proliferation, the sample comprising one or more isoforms of the α subunit of Na, K-ATPase; and
if the ratio is ≥0.3, ≥0.5, ≥1, or ≥10, indicating administration to the subject a composition comprising cardiac glycoside.

Yet another aspect of the invention provides a method of treating, in a subject, a disease or disorder having an etiology associated with excessive cell proliferation with a composition comprising cardiac glycoside, the method comprising:
obtaining a sample of diseased tissue from the subject, the disease having an etiology associated with excessive cell proliferation and the sample comprising one or more isoforms of the α subunit of Na, K-ATPase;
requesting that the ratio of α3 isoform to α1 isoform of the α subunit of Na, K-ATPase in the sample be determined; and
indicating administration to the subject a composition comprising cardiac glycoside if the ratio is ≥0.3, ≥0.5, ≥1, or ≥10.

Yet another aspect of the invention provides a method of determining whether or not a subject having a disease or disorder having an etiology associated with excessive cell proliferation should be treated with a cardiac glycoside, the method comprising:
obtaining a sample of diseased tissue from the subject, the disease having an etiology associated with excessive cell proliferation, the sample comprising one or more isoforms of the α subunit of Na, K-ATPase;
determining the ratio of α3 isoform to α1 isoform of the α subunit of Na, K-ATPase in the sample; and
if the ratio is ≥0.3, ≥0.5, ≥1, or ≥10, indicating that the subject should be treated with cardiac glycoside by administration of a composition comprising cardiac glycoside to the subject according to a prescribed dosing regimen, or
if the ratio is <0.3, indicating that the subject should not be treated with cardiac glycoside for treatment of the disease or disorder having an etiology associated with excessive cell proliferation.

Some embodiments of the invention include those wherein: 1) the subject is prescribed and administered a therapeutically relevant dose of composition comprising cardiac glycoside; 2) the subject is administered the composition comprising cardiac glycoside according to a prescribed dosing regimen; 3) the subject is administered a composition comprising an extract comprising a cardiac glycoside; 4) the extract further comprises one or more other therapeutically effective agents; 5) the composition further comprises one or more other therapeutically effective agents; 6) the subject is administered a hot water extract of a plant or animal source containing cardiac glycosides 2 mg to 22.5 mg per day; or 7) a concentrated extract (e.g. supercritical $CO_2$ extract) of a plant or animal source of cardiac glycosides ranging from 0.6 to 4.8 mg; or 8) a pure single chemical form of a cardiac glycoside ranging from 10 to 500 ug.

The individual steps of the methods of the invention can be conducted at separate facilities or within the same facility.

The invention includes all combinations of the aspects, embodiments and sub-embodiments of the invention disclosed herein.

BRIEF DESCRIPTION OF THE FIGURES

The following figures form part of the present description and describe exemplary embodiments of the claimed invention. The skilled artisan will, in light of these figures and the description herein, be able to practice the invention without undue experimentation.

FIGS. 6A-6F depict photographs of immunohistochemically stained normal skin cells from DI 13782.

FIGS. 7A-7H depict photographs of immunohistochemically stained melanoma skin cells: FIGS. 7A-7B depict DI 15041 cells; FIGS. 7C-7D depict DI 15832 cells; FIGS. 7E-7F depict DI 15833 cells; FIGS. 7G-7H depict DI 15834 cells.

DETAILED DESCRIPTION OF THE INVENTION

Figure 1A:
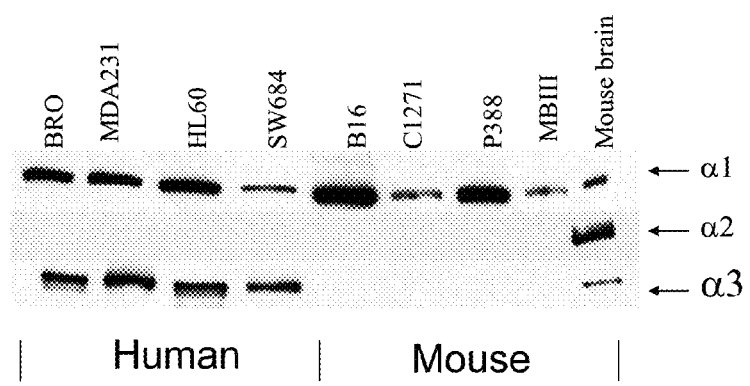
FIG. 1A depicts a photograph of the relevant bands of a gel electropherogram obtained as part of a Western blot analysis of human and mouse cell lines for relative quantitation of the α1 and α3 isoforms of the α-subunit of Na, K-ATPase.

The invention provides a method of predicting whether or not a subject suffering from a disease or disorder having an etiology associated with excessive cell proliferation will receive a clinical benefit against that disease or disorder by treatment of the subject with a cardiac glycoside-containing composition. The method is used to determine whether or not the disease or disorder in the subject will be therapeutically responsive to treatment with a cardiac glycoside-containing composition. In other words, the method is used to determine the probability of a therapeutic response in the subject following treatment thereof with a therapeutically relevant dose (or effective dose) of one or more cardiac glycosides according to a prescribed dosing regimen.

In brief, a sample is obtained from diseased tissue in a subject. The sample comprises one or more isoforms of the α subunits of Na, K-ATPase from the diseased tissue and is assayed as described herein to determine the relative amounts or concentrations of α3 and α1 isoforms of the α subunit of the Na, K-ATPase. The ratio of the relative amounts or concentrations of the subunits is then calculated. If the ratio of α3 isoform to α1 isoform is greater than or equal to 0.3, the method predicts an increased probability that the disease or disorder will be therapeutically responsive to treatment with a cardiac glycoside. For example, if the ratio is from 0.3-0.45+/−0.05, there is at least a 20% or a 20% to less than 30% probability that the disease or disorder will respond to treatment with the cardiac glycoside. If the ratio is less than 0.2 or less than 0.3, the method predicts a less than 20% probability that the disease or disorder will be therapeutically responsive to treatment with cardiac glycoside. In general, the higher the ratio, the greater the probability is of a therapeutic response. For example, if the ratio is from 0.5-0.95+/−0.05, there is at least a 30% or a 30% to 50% probability that the disease or disorder will respond to treatment with the cardiac glycoside. If the ratio is from greater than or equal to 1+/−0.05, there is at least a 50% probability that the disease or disorder will respond to treatment with the cardiac glycoside. If the ratio is from greater than 10+/−0.05, there is at least a 75% probability that the disease or disorder will respond to treatment with the cardiac glycoside.

By "therapeutically responsive" is meant that a subject suffering from the disease or disorder will enjoy at least one of the following clinical benefits as a result of treatment with a cardiac glycoside: amelioration of the disease or disorder, reduction in the occurrence of symptoms associated with the disease or disorder, partial remission of the disease or disorder, full remission of the disease or disorder, or increased time to progression. In other words, the therapeutic response can be a full or partial therapeutic response, and the method is used to determine the probability of a therapeutic response, regardless of whether it is a full or partial response.

As used herein, "time to progression" is the period, length or duration of time after a disease is diagnosed (or treated) until the disease begins to worsen (such as until a tumor begins or continues to grow). It is the period of time during which the level of a disease is maintained without further progression of the disease, and the period of time ends when the disease begins to progress again. Progression of a disease is determined by "staging" a subject suffering from a cell proliferative disease prior to or at initiation of therapy. For example, the size, location and number of tumors a subject has is determined prior to or at initiation of therapy. The subject is then treated with cardiac glycoside, and the size and number of tumors are monitored periodically. At some later point in time, the size and/or number of tumors may increase, thus marking progression of the disease and the end of the "time to progression". The period of time during which the disease did not progress or during which the level or severity of the disease did not worsen is the "time to progression".

It should be noted that a therapeutic response can be a full or partial response at therapeutically relevant doses to a subject according to a prescribed dosing regimen. In other words, the level of predicted therapeutic response is determined at a dose that would not be fatal to a subject to which the cardiac glycoside is administered. A therapeutically relevant dose, therefore, is a therapeutic dose according to a prescribed dosing regimen at which a therapeutic response of the disease or disorder to treatment with a cardiac glycoside is observed and at which a subject can be administered the cardiac glycoside without an excessive amount of unwanted or deleterious side effects. A therapeutically relevant dose is non-lethal to a subject, even though it may cause some side effects in the patient. It is a dose at which the level of clinical benefit to a subject being administered the cardiac glycoside exceeds the level of deleterious side effects experienced by the subject due to administration of the cardiac glycoside. A therapeutically relevant dose will vary from subject to subject according to a variety of established pharmacologic, pharmacodynamic and pharmacokinetic principles. However, a therapeutically relevant dose (relative, for example, to oleandrin) will typically not exceed 10, 25, 100, 250, 500 or 1000 micrograms of cardiac glycoside/day or it can be in the range of 10-500, 25-500, 10-1000 or 25-1000 micrograms of cardiac glycoside/day or 2 mg to 22.5 mg of cardiac glycoside per day. Therefore, the method of the invention is used to predict therapeutic responsiveness of the disease or disorder when a subject is administered a therapeutically relevant dose according to a prescribed dosing regimen. It is known in the art that the actual amount of a drug required to provide a target therapeutic result in a subject may vary from subject to subject according to the basic principles of pharmacy.

A therapeutically relevant dose can be administered according to any dosing regimen typically used in the treatment of diseases or disorders having an etiology associated with excessive cell proliferation. The therapeutically relevant dose is administered according to a prescribed dosing regimen, which can be modified as need according to a subject's clinical response. A therapeutically relevant dose can be administered once, twice, thrice or more daily. It can be administered every other day, every third day, every fourth day, semiweekly, weekly, biweekly, every three weeks, every four weeks, monthly, bimonthly, semimonthly, every three months, every four months, semiannually, annually, or according to a combination of any of the above. For example, a therapeutically relevant dose can be administered once daily for one or more weeks. A prescribed dosing regimen is a dosing regimen prescribed by a caregiver, such as a clinician, specifying the frequency of administration of therapeutically relevant doses throughout a treatment period and specifying the duration of such treatment period. For example, a prescribed dosing regimen can include repeated administration of one or more predetermined therapeutically relevant doses at specified time intervals for a specified treatment period. The therapeutically relevant dose, predetermined time interval and treatment period can be changed dependently or independently of one another as needed and as determined by a caregiver.

By "lysis composition" is meant one or more agents capable of lysing the membrane of a cell to form a cell lysate or complete dissolution of cellular contents. The lysis composition can comprise one or more of the following: aqueous liquid medium, buffering agent, salt, chelating agent, surfactant, anti-foaming agent, protease inhibitor, and phosphatase and ATPase inhibitor.

As used herein in relation to the kit, a "positive control sample" comprises a quantifiable amount or concentration of $\alpha 3$ subunit isoform of Na, K-ATPase. The positive control can further comprise a quantifiable amount or concentration of $\alpha 1$ subunit isoform of Na, K-ATPase. The quantifiable amounts or concentrations of each subunit isoform independently can be predetermined or known. The amount or concentration of subunit isoform will be sufficient to provide a positive response for presence of the subunit isoform as determined according to the particular method used in an assay for which it is a positive control. For example, in a Western blot assay, the amount or concentration of subunit isoform in the positive control will be sufficient to bind with a corresponding antibody such that when the subunit presence is determined, for example by densitometric or radiometric determination, a positive response for the presence of the subunit isoform will be obtained. For the immunohistochemical staining assay (such as detailed in Example 27), the amount or concentration of subunit isoform in the positive control will be sufficient to permit facile visualization and quantitation when applied to a gel, separated from other proteins using electrophoresis and then stained with the use of primary and secondary antibodies as previously described or when applied to quantitative analysis under microscopic examination using digital image capture and quantitative image analysis software. If the amount or concentration of subunit isoform in the control sample is known or predetermined prior to analysis, the level of positive response can be related to the amount or concentration so as to provide a calibration curve for the subunit isoform.

If $\alpha 3$ subunit isoform of Na, K-ATPase is present in the positive control sample, the ratio of $\alpha 3$ isoform to $\alpha 1$ isoform will generally be within the range of 0.3 to 100 or greater. Suitable ranges for the ratio also include 0.3 to 0.5, 0.5 to 1.0, 1.0 to 20, and 20 to 100.

As used herein in relation to the kit, a "negative control sample" comprises an amount or concentration of $\alpha 1$ subunit isoform of Na, K-ATPase but excludes the $\alpha 3$ subunit isoform of Na, K-ATPase. The amount or concentration of $\alpha 1$ subunit isoform will be sufficient to provide a positive response for presence of the isoform as determined according to the particular method used in an assay, such as the Western blot assay, in which it is used as a negative control. The amount or concentration can be known or predetermined and, if so, can be used to develop a calibration curve for the isoform.

As part of a validation of the method and kit of the invention, the inventors conducted preclinical evaluations of a cardiac glycoside-containing composition for the treatment of various cancer and tumor phenotypes. The evaluation was conducted using in vivo, ex-vivo, in vitro and in xenograft animal models. For each phenotype evaluated, a cellular sample of tissue or cell mass was analyzed as described herein to determine the ratio of $\alpha 3$ subunit isoform of Na, K-ATPase to $\alpha 1$ subunit isoform of Na, K-ATPase. A correlation between the phenotypes that are responsive to cardiac glycoside treatment and the ratio of $\alpha 3$ subunit isoform of Na, K-ATPase to $\alpha 1$ subunit isoform of Na, K-ATPase for each of the phenotypes in a number of human tumor cell lines was observed. It was concluded that a therapeutically responsive cancer or tumor phenotype (or one with an increased probability of a therapeutic response) possesses a ratio of $\alpha 3$ subunit isoform of Na, K-ATPase to $\alpha 1$ subunit isoform of Na, K-ATPase of at least 0.3.

Figure 1B:
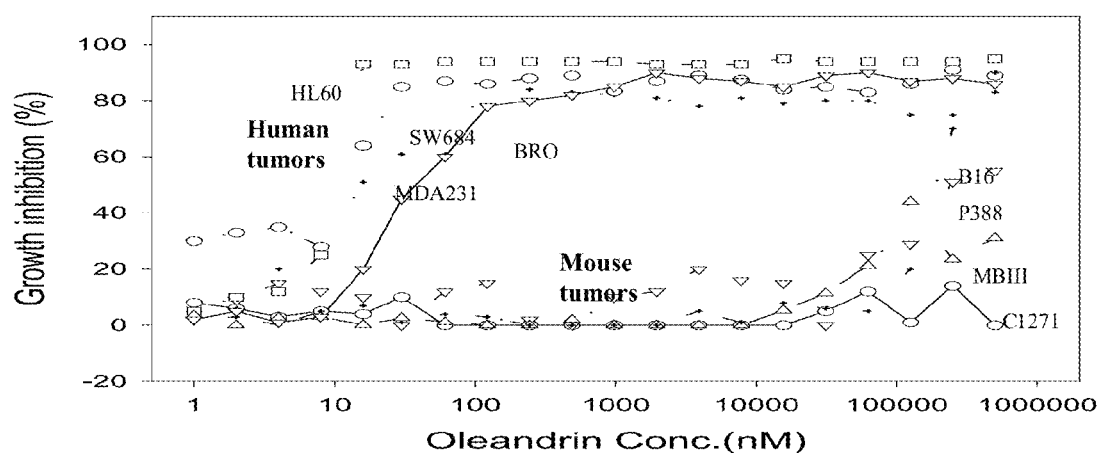
FIG. 1B depicts a plot of concentration of oleandrin (nM) versus percent of cell growth inhibition for human and mouse tumors.

Rodent (rat or mouse) cancer cells can be used as a negative control sample. FIG. 1A depicts a film developed against the gel of a Western blot analysis of rodent tumor cell lines. The inventors' data demonstrate that all rodent (mouse and rat) tumor cell lines tested to date lack the $\alpha 3$ subunit isoform and that their proliferation in vitro is not significantly inhibited by incubation with cardiac glycosides (e.g. ouabain, oleandrin, bufalin, etc.). Human tumor cell lines are generally more sensitive to treatment with cardiac glycoside-containing composition than are murine tumor cells (FIG. 1B). The inventors believe this difference in therapeutic responsiveness is due to the differences in the ratio of $\alpha 3$ to $\alpha 1$ isoforms in the two different species, as noted above.

It should be noted that the antibodies against $\alpha 3$ isoform can be derived from a number of different vendors including Affinity Bioreagents (Golden, Colo.), Novus (Littleton, Colo.) or Sigma Chemical Co. (St Louis, Mo.) all of which showed equal reactivity (i.e. binding) to the $\alpha 3$ epitope (isoforms) in a positive control sample.

Figure 2:
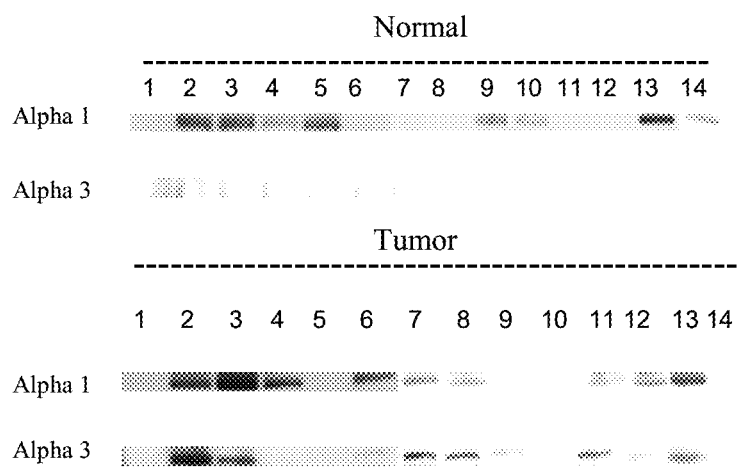
FIG. 2 depicts a photograph of the relevant bands of gel electropherograms obtained as part of a Western blot assay of normal and malignant human colon cells

In humans, the $\alpha 3$ to $\alpha 1$ isoform ratio for the $\alpha$ subunit of Na, K-ATPase may vary according to the source and state of malignancy of the tissue. Tissue samples from normal and malignant colon tissue were taken from each subject for a total of fourteen individual subjects. The $\alpha 3$ to $\alpha 1$ isoform ratio for each tissue sample was determined as described herein. The data in FIG. 2 and the table below demonstrate a relative lack of $\alpha 3$ isoform in normal tissues, and the presence of α3 isoform in approximately 66-70% of malignant tissues. Both normal and malignant tissues contain the α1 subunit isoform.

| Subject | Normal colon tissues α3/α1 ratio | Colon tumor tissues α3/α1 ratio |
|---|---|---|
| 1 | 0.0 | 0.0 |
| 2 | 0.02 | 0.64 |
| 3 | 0.03 | 0.07 |
| 4 | 0.01 | 0.04 |
| 5 | 0.03 | 0.0 |
| 6 | 0.0 | 0.56 |
| 7 | 0.0 | 3.4 |
| 8 | 0.0 | 6.0 |
| 9 | 0.0 | 100.0 |
| 10 | 0.0 | 0.0 |
| 11 | 0.0 | 6.2 |
| 12 | 0.0 | 0.83 |
| 13 | 0.0 | 0.36 |
| 14 | 0.0 | 0.00 |

The α3 to α1 isoform ratio for the α subunit of Na, K-ATPase was determined for various different human cancer and tumor phenotypes in cultured cell lines as well as actual tumor biopsy samples. In addition, the relative sensitivity of each phenotype to treatment with a cardiac glycoside-containing composition was determined using data derived from in vitro cell culture experiments. The data for an oleandrin-containing composition are detailed in the following table and FIG. 3A.

| Cell line | Tumor type | α3/α1 | In vitro response to oleandrin? | $IC_{50}$ (nM) |
|---|---|---|---|---|
| MDA231 | Breast | 0.01 | No* | N/A |
| BXPC3 | Pancreas | 0.29 | No* | N/A |
| MCF7 | Breast | 0.2 | No* | N/A |
| SUM149 | Breast | 0.3 | Partial** | 22.5 |
| HCT116 | Colon | 1.7 | Partial** | 36.2 |
| MiaPaca | Pancreas | 1.5 | Complete*** | 14.2 |
| CACO2 | Colon | 4.6 | Complete*** | 9.4 |
| HT29 | Colon | 6.8 | Complete*** | 15.6 |
| LS174T | Colon | 7.6 | Complete*** | 20.7 |
| BRO | Melanoma | 11.5 | Complete*** | 8.2 |
| DOD-1 | Colon | 19.8 | Complete*** | 19.6 |
| PANC1 | Pancreas | 60 | Complete*** | 6.1 |
| BXPC3 | Pancreas | 0.29 | No* | N/A |
| MiaPaca | Pancreas | 1.5 | Complete*** | 2.1 |
| PANC1 | Pancreas | 60 | Complete*** | 1.2 |

*Denotes less than 50% growth inhibition achieved at concentrations up to 125 nM
**Denotes greater than 50% but less than 75% growth inhibition achieved at 62 nM
***Denotes greater than 75% growth inhibition achieved at 62 nM As defined in the Tables above, an "in vitro response" denotes the extent to which proliferation of a given tumor cell line is inhibited with a stated concentration of drug (cardiac glycoside) over a defined period of time. A designation of "no response" denotes less than 50% growth inhibition at any of the multiple drug concentrations tested. That is, no concentration could be identified as an $IC_{50}$ value (that concentration producing inhibition of cell growth by 50% over the stated period of time of the experiment). Accordingly, were this tumor cell line growing in a mammal such as a human, it is probable that the drug would be ineffective in producing significant inhibition of tumor growth. The designation of "partial response" in the Table above denotes the capacity of a given cardiac glycoside such as oleandrin or bufalin to inhibit cell proliferation by more than 50% but less than 75% relative to nontreated tumor cell growth. Accordingly, this would equate to a partial or less than complete therapeutic response of the tumor to the cardiac glycoside if this product were used to treat tumor growth in a mammal such as a human. Finally, the designation of "complete response" in the Table above denotes greater than a 75% inhibition of tumor cell proliferation relative to untreated tumor cell populations. Accordingly, it is probable that total inhibition of tumor growth (or a complete therapeutic response, in a mammal might be achieved.

Based upon the isoform ratio data above, the method predicts: 1) MDA231, BXPC3 and MCF7 cell lines would be substantially non-responsive to treatment with a therapeutically relevant amount of cardiac glycoside; 2) SUM149 and HCT116 cell lines would exhibit at least a partial response to treatment with a therapeutically relevant amount of cardiac glycoside; and 3) CACO2, HT29, LS174T, BRO, DOD-1 and PANC1 cell lines would exhibit a full therapeutic response to treatment with a therapeutically relevant amount of cardiac glycoside.

Figure 3A:
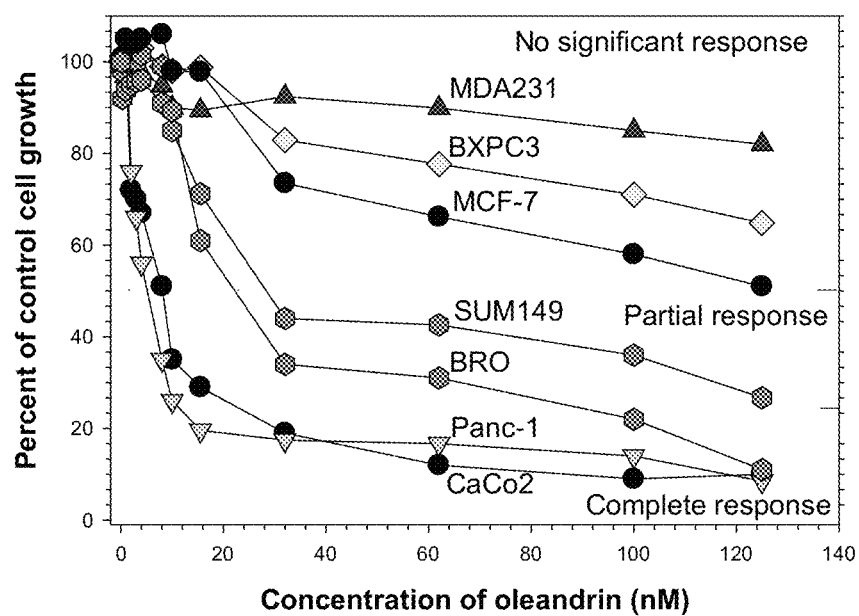
FIG. 3A depicts a plot of concentration of oleandrin (nM) versus percent of cell growth inhibition for various different tumor cell lines varying in their relative expressions of the α1 and α3 isoforms of Na, K-ATPase subunits.
Figure 3B:
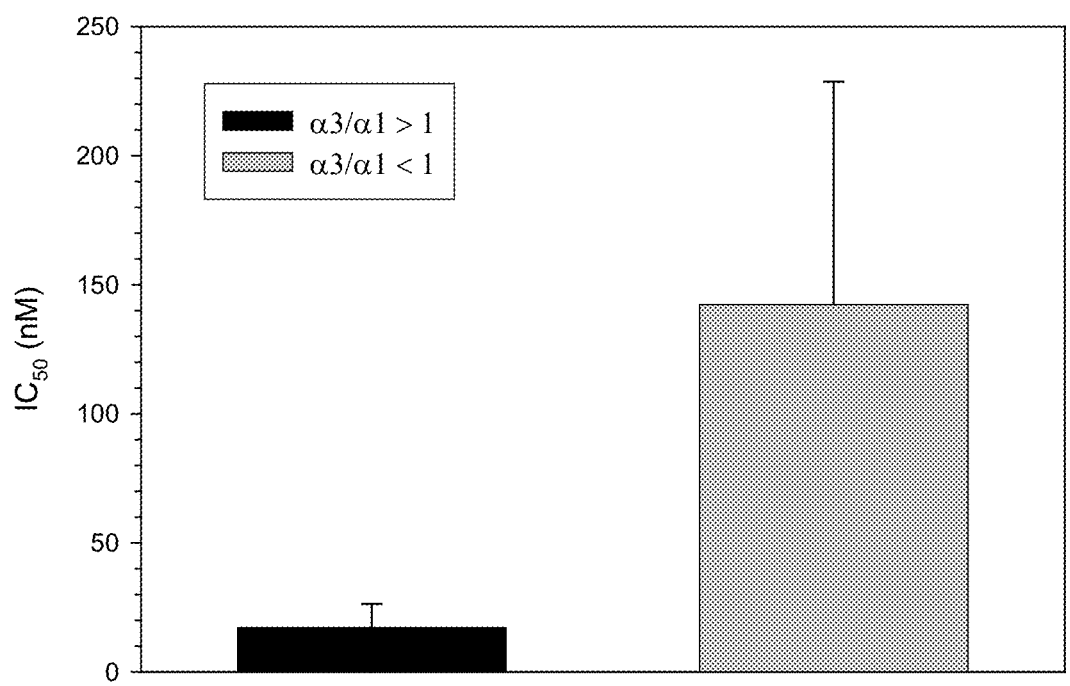
FIG. 3B depicts a bar chart of the mean $IC_{50}$ of oleandrin for cell growth inhibition in two different groups of tumor cell lines: a first group having an α3 to α1 subunit isoform ratio of greater than one; and a second group having an α3 to α1 subunit isoform ratio of less than one.

FIG. 3A depicts a plot of concentration (nM) of oleandrin (provided as oleandrin) versus the percentage of growth of control. The data demonstrate that the cell lines evaluated can be categorized into three different groups according to their response to cardiac glycoside treatment as determined by relative inhibition of proliferation of the human tumor cell lines: Group I—cells that undergo less than 50% growth inhibition achieved at concentrations up to 125 nM of cardiac glycoside; Group II—cells that undergo greater than or equal to 50% growth inhibition achieved at concentrations up to 62 nM of cardiac glycoside; and Group III—cells that undergo greater than or equal to 75% growth inhibition achieved at concentrations up to 62 nM of cardiac glycoside. Exemplary cell lines for the groups are: Group I—MDA231, BXPC3, MCF-7; Group II—SUM149, BRO; Group III—Panc-1, CaCo2. The response data are as predicted by the isoform ratio data. In order to establish the robustness of the method and kit of the invention, a statistical analysis of cellular response data was conducted. The data in FIG. 3B depict the relative ability of oleandrin-containing composition to inhibit human tumor cell proliferation in vitro. The data are depicted as Mean±SD. Oleandrin mediated growth inhibition was examined in ten cell lines (representing a variety of solid tumors) in which the relative subunit content α3/α1 isoform ratio >1.0 and six cell lines in which the α3/α1 isoform ratio <1.0. The data show that there is an 8-fold (800%) difference between these groups. That is, in those cell lines in which the α3/α1 isoform ratio ≥1.0, oleandrin was found to be a much more effective drug as compared to those in which the α3 subunit isoform was only poorly expressed. The data prove that the ratio of α3/α1 subunit isoforms can be used to predict the responsiveness of a cancer or tumor cell line to treatment with a cardiac glycoside-containing composition.

Figure 4A:
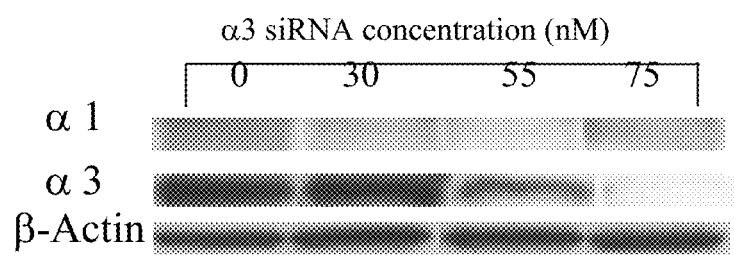
FIG. 4A depicts a photograph of the relevant bands of a gel electropherogram obtained as part of a Western blot assay of non-transfected and transfected human tumor cells.
Figure 4B:
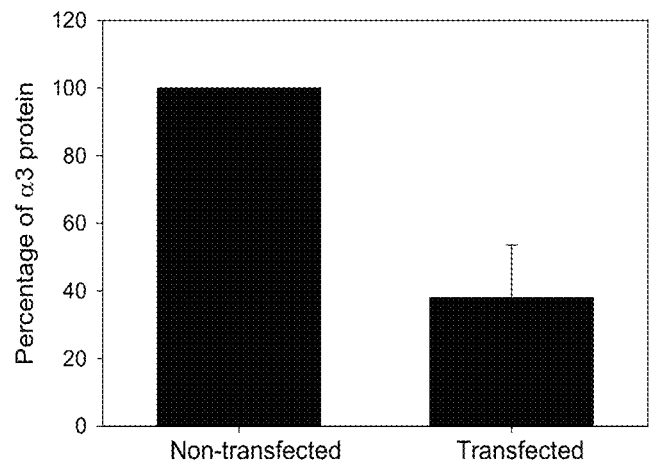
FIG. 4B is a bar chart demonstrating the relative expression of the α3 isoform in the non-transfected and transfected cells of FIG. 4A.
Figure 4C:
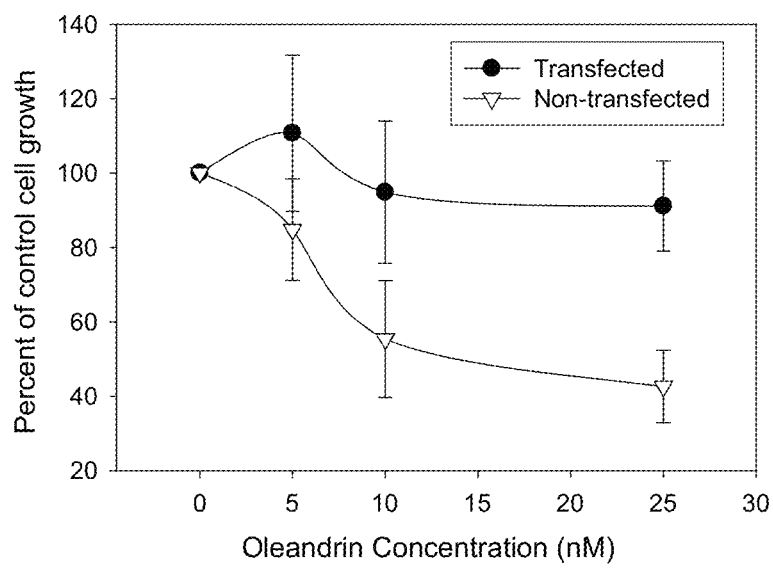
FIG. 4C depicts a plot of concentration of oleandrin (nM) versus percent of cancer cell growth inhibition for the cells of FIG. 4A.

Further proof of the relative importance of the α3/α1 isoform ratio toward predictability of a therapeutic response by a target malignant tissue to treatment with a cardiac glycoside was established as follows. Artificial down-regulation of the expression of α3 isoform in human pancreatic cancer cells, i.e. manipulation of isoform content of subunits of Na, K-ATPase, was achieved by transfection of cells with siRNA (silencing RNA) specific to the α3 isoform. The data demonstrate a decline in expression of the α3 isoform (as determined by Western blot (FIG. 4A)). Quantitation of the decreased expression of α3 by Western blot is detailed in FIG. 4B. FIG. 4C demonstrates that the transfected cells, in which the α3 expression has been reduced, lose their sensitivity to treatment with oleandrin.

Figure 5A:
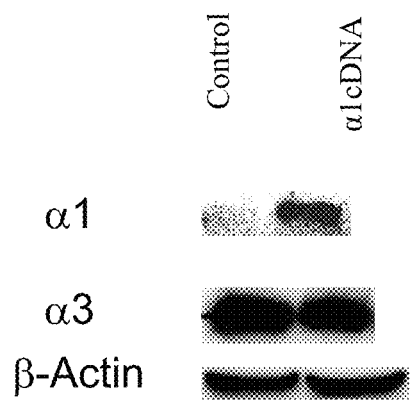
FIG. 5A depicts a photograph of the relevant bands of a gel electropherogram obtained as part of a Western blot assay of non-transfected and transfected Panc-1 cells.
Figure 5B:
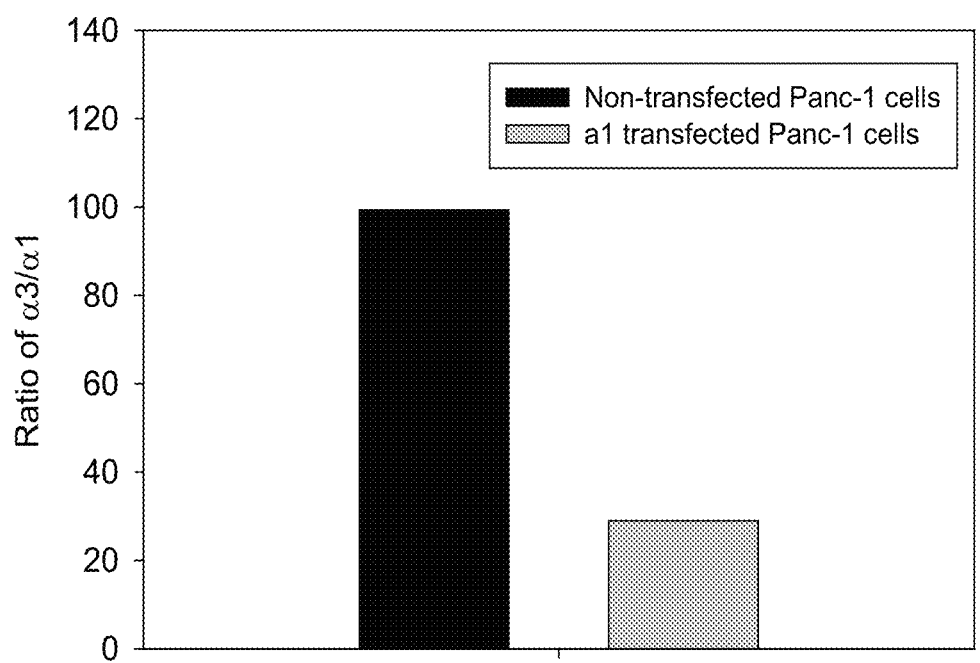
FIG. 5B is a bar chart demonstrating the relative expression of the α3 isoform in the non-transfected and transfected cells of FIG. 5A.
Figure 5C:
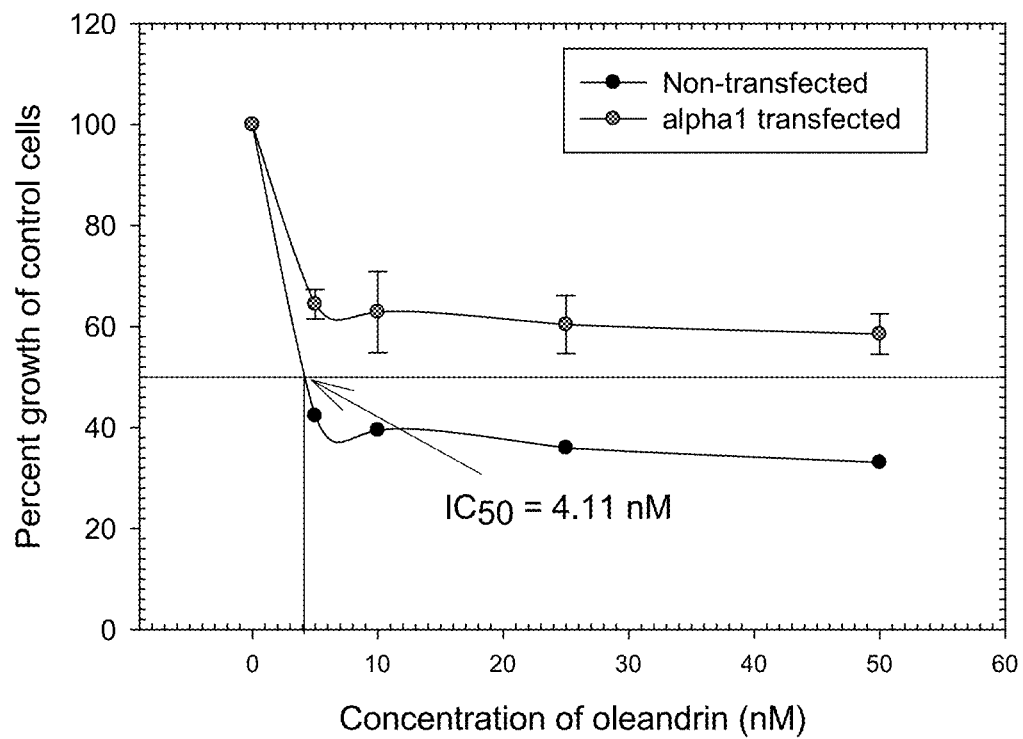
FIG. 5C depicts a plot of concentration of oleandrin (nM) versus percent of cancer cell growth inhibition for the cells of FIG. 5A.

Still further proof of the relative importance of the α3/α1 isoform ratio toward predictability of a therapeutic response by a target malignant tissue to treatment with a cardiac glycoside was established by transfection of Panc-1 cells with α1 subunit isoform. The Na, K-ATPase α1 subunit isoform was transfected to Panc-1 cells, which normally lack α1 expression. The control sample in FIG. 5A is for non-transfected Panc-1 cells, and the α1cDNA sample in FIG. 5A is for Panc-1 cells transfected with the α1 subunit isoform. As a result, the ratio of α3 to α1 was reduced in the transfected Panc-1 cells (FIG. 5B). The sensitivity of the transfected Panc-1 cells to oleandrin treatment was then evaluated. The sensitivity of these transfected cells to oleandrin treatment was reduced as evidenced by the shift of IC50 value of oleandrin from 4.1 nM of non-transfected Panc-1 cells to more than 50 nM in α1 transfected cells (FIG. 5C). Accordingly, the antiproliferative activity of oleandrin was markedly reduced in Panc-1 cells transfected with the α1 subunit isoform.

Detection and quantitation of the α3 and α1 isoforms of the Na, K-ATPase subunit can also be accomplished by immunohistochemical staining, such as detailed in Example 27. Cells are immunohistochemically stained such that the α3 and α1 isoforms are stained differentially. The content of each isoform type is quantified and the ratio of content of the α3 to α1 isoform is determined. Differential immunohistochemical staining of the α3 and α1 isoforms can be accomplished by various means. In some embodiments, a tissue sample is stained with two different stains, one stain being used selectively or specifically for the α3 isoform and the other stain being used selectively or specifically for the α1 isoform. In some embodiments, two close but different samples are obtained from the same tissue and stained, such that the first sample is treated to stain the α3 isoform and the second sample is treated to stain the α1 isoform. The amounts of the α3 and α1 isoforms are then quantified, and the ratio of α3 isoform to α1 isoform is then determined. Based upon the ratio, a prediction is made as to the likelihood of a therapeutic response of the tissue to treatment with cardiac glycoside.

Quantitation of the α3 isoform and the α1 isoform of the Na, K-ATPase subunit in an immunohistochemically stained sample (cell or tissue slide) can be accomplished through manual or automated procedures. These include but are not limited to individual grading of staining intensity of set areas of suitably stained slides (e.g. using visual observations of relative staining intensities (e.g. intensities of 0-5 where 0 is no detectable staining and 5 represents intense staining), then compiling average staining intensities of a set number of examined regions and comparing relative staining of α3 staining to that of slides stained for α1, and calculating the ratio of α3 to α1 in the sample. Another manner in which quantitation of the relative staining of α1 and α3 (i.e. the ratio of α3 to α1 present in a sample) can be accomplished through the use of microscopic examination of set areas of stained slides and the use of digital analysis software to determine relative staining intensities. Likewise, computer assisted digital video analysis can also be performed to determine relative isoform staining and to compute a ratio of α3 to α1 staining intensities, thereby determining the ratio of α3 isoform to α1 isoform content in the sample.

For example, FIGS. 6A-6F depict photographs of normal skin cells from DI 13782. FIGS. 6A, 6C and 6E depict α subunit of $Na^+/K^+$ATPase immunoreactivity (immunohistochemically stained). FIGS. 6B, 6D and 6F depict photographs of the corresponding non-immune (control) IgG incubated sections. Strong 2+ or 3+ levels of immunoreactivity were seen in all donors of normal skin. The squamous epithelium, hair follicle epithelium, basement membrane of the sebaceous glands, sweat coils and mononuclear lymphocytes in blood vessels were all positively stained. Pyloerector muscle was weakly immunoreactive.

FIGS. 7A-7H depict photographs of melanoma cells. FIGS. 7A, 7C, 7E and 7G depict α subunit of $Na^+/K^+$ ATPase immunoreactivity (immunohistochemically stained). FIGS. 7B, 7D, 7F and 7H depict the corresponding non-immune (control) IgG incubated sections. FIGS. 7A and 7B depict DI 15838 cells. FIGS. 7C and 7D depict DI 15840 cells. FIGS. 7E and 7F depict DI 15842 cells. FIGS. 7G and 7H depict DI 15844 cells. All BCC samples were positive for the α subunit of $Na^+/K^+$ATPase with varying degrees of intensity. All immunoreactivity was localized to the nuclei and cytoplasm of the tumor cells. Following differential immunohistochemical staining of the tissues, the ratio of α3 subunit isoform to α1 subunit isoform can be determined and a prediction as to therapeutic responsiveness to treatment with cardiac glycoside can be made.

The relevance of the method of the instant invention toward another cardiac glycoside was evaluated. Huachansu is a toad skin extract containing cardiac glycosides known as bufadienolides. The therapeutic responsiveness of two human pancreatic cell lines (SW1990 and Panc-1) to treatment with huachansu was evaluated. Based upon the data in the tables above, one would predict that SW 1990 cell would not be but that Panc-1 cells would be therapeutically responsive to huachansu. The response data provided the expected results.

The examples below include evidence of the efficacy of cardiac glycosides in treating cancer and tumor related diseases and disorders. Example 21 includes a case history for treatment of a patient presenting with metastatic pancreatic gastrinoma. The prognostic assay, methods and kit of the invention can be used in combination with one or more other prognostic or diagnostic assays, methods and kits known in the art of diseases or disorders having an etiology associated with excessive cell proliferation. For example, if a clinician intends to treat a subject having cancer or tumor with a combination of a cardiac glycoside and another chemotherapeutic agent or radiation therapy, and it is known that the particular phenotype of cancer or tumor, which the subject has, is at least partially therapeutically responsive to treatment with said other chemotherapeutic agent or radiation therapy, then the present invention can be used to determine the probability of at least a partial therapeutic response of the cancer or tumor in the subject when treated with cardiac glycoside. If the results indicate that there is an increased probability that the cancer or tumor will be therapeutically responsive to treatment with cardiac glycoside, the clinician can then prescribe and/or administer treatment of the cancer or tumor with the cardiac glycoside and other therapeutic agent or radiation therapy or a combination thereof.

The cardiac glycoside can be any cardiac glycoside known to possess therapeutic activity in the treatment of a disease or disorder having an etiology associated with excessive cell proliferation. The cardiac glycoside can be present in pure form or as a mixture with one or more other compounds. The cardiac glycoside can be present as an extract. The extract can be prepared by supercritical fluid (SCF) carbon dioxide ($CO_2$) extraction or a chemically modified form of such an extract (e.g. an extract that includes ethanol or was made using SCF $CO_2$ and ethanol). The extract can be obtained from plant or animal material. The animal material can be the exudate of a toad (e.g. *Bufo bufo*). The plant material can be plant mass such as obtained from *Nerium* species, such as *Nerium oleander*, or of *Thevetia* species, such as *Thevetia neriifolia* or *Thevetia puruviana* (otherwise known as yellow oleander). The extraction process can be conducted on a dried powder of *Nerium oleander* leaves prepared according to a process described in a currently U.S. provisional application Ser. No. 60/653,210 filed Feb. 15, 2005 in the name of Addington or U.S. application Ser. No. 11/340,016 filed Jan. 26, 2006 in the name of Addington, U.S. application Ser. No. 11/191,650 filed Jul. 28, 2006 (now U.S. Pat. No. 7,402,325 issued Jul. 22, 2008) in the name of Addington, or PCT International Patent Application No. PCT/US06/29061 filed Jul. 26, 2006, the entire disclosures of which are hereby incorporated by reference, or by a process described herein.

As used herein, the term "oleandrin" is taken to mean all known forms of oleandrin unless otherwise specified. Oleandrin can be present in racemic, optically pure or optically enriched form. *Nerium oleander* plant material can be obtained, for example, from commercial plant suppliers such as Aldridge Nursery, Atascosa, Tex.

The extract can be obtained by modified (e.g. ethanol) or unmodified supercritical fluid extraction of a cardiac glycoside-containing plant mass. The supercritical fluid extract can comprise at least one other pharmacologically active agent that contributes to the therapeutic efficacy of the cardiac glycoside when the extract is administered to a subject. It can contribute additively or synergistically to the therapeutic efficacy of the cardiac glycoside.

The extract can be prepared by various different processes. The extract can be prepared according to the process developed by Dr. Huseyin Ziya Ozel (U.S. Pat. No. 5,135,745) describes a procedure for the preparation of the extract of the plant in water. The aqueous extract reportedly contains several polysaccharides with molecular weights varying from 2KD to 30KD, oleandrin and oleandrigenin, odoroside and neritaloside. The polysaccharides reportedly include acidic homopolygalacturonans or arabinogalaturonans. U.S. Pat. No. 5,869,060 to Selvaraj et al. discloses hot water extracts of *Nerium* species and methods of production thereof. The resultant extract can then be lyophilized to produce a powder. U.S. Pat. No. 6,565,897 (U.S. Pregrant Publication No. 20020114852 and PCT International Publication No. WO 2000/016793 to Selvaraj et al.) discloses a hot-water extraction process for the preparation of a substantially sterile extract. Erdemoglu et al. (*J. Ethnopharmacol.* (2003) November 89(1), 123-129) discloses results for the comparison of aqueous and ethanolic extracts of plants, including *Nerium oleander*, based upon their anti-nociceptive and anti-inflammatory activities. Organic solvent extracts of *Nerium oleander* are disclosed by Adome et al. (*Afr. Health Sci.* (2003) August 3(2), 77-86; ethanolic extract), el-Shazly et al. (*J. Egypt Soc. Parasitol.* (1996), August 26(2), 461-473; ethanolic extract), Begum et al. (*Phytochemistry* (1999) February 50(3), 435-438; methanolic extract), Zia et al. (*J. Ethnolpharmacol.* (1995) November 49(1), 33-39; methanolic extract), and Vlasenko et al. (*Farmatsiia.* (1972) September-October 21(5), 46-47; alcoholic extract). U.S. Pregrant Patent Application Publication No. 20040247660 to Singh et al. discloses the preparation of a protein stabilized liposomal formulation of oleandrin for use in the treatment of cancer. U.S. Pregrant Patent Application Publication No. 20050026849 to Singh et al. discloses a water soluble formulation of oleandrin containing a cyclodextrin. U.S. Pregrant Patent Application Publication No. 20040082521 to Singh et al. discloses the preparation of protein stabilized nanoparticle formulations of oleandrin from the hot-water extract.

The SCF extraction can be conducted in the presence of a modifier in the supercritical fluid, such as ethanol, to enhance extraction of the desired compound(s) from the plant mass. Modifiers generally possess volatility between that of the supercritical fluid and of the compound being extracted, and they must be miscible with the supercritical fluid. In some embodiments, the modifier is a liquid at ambient conditions. By way of example and without limitation, a modifier can be selected from the group consisting of ethanol, methanol, propanol, acetone, ethyl acetate, methylene chloride, etc.

The extract is a mixture of pharmacologically active compounds, such as oleandrin or other cardiac glycosides, oleaside, and other plant materials. Oleandrin extract from a supercritical fluid process contains by weight a theoretical range of 0.9% to 2.5% oleandrin. SCF extracts comprising varying amount of oleandrin have been obtained. In one embodiment, the SCF extract comprises about 2% by wt. of oleandrin.

As evidenced by the data herein, the SCF extract comprises a mixture of various components. Some of those components include oleandrin, oleaside A, oleandrigenin, neritaloside, odorside (Wang X, Plomley J B, Newman R A and Cisneros A. LC/MS/MS analyses of an oleander extract for cancer treatment, *Analytical Chem.* 72: 3547-3552, 2000), and other unidentified components. The SCF extractable unidentified components of the SCF extract appear to include at least one other pharmacologically active component that contributes to the efficacy of the oleandrin in the SCF extract. That is, at least one other SCF extractable component functions additively or synergistically with the oleandrin to provide the observed efficacy.

It is possible that the extracts also differ in their relative performance as determined by efficacy against several tumor cell lines. Even so, if a cardiac glycoside is present in a sufficiently high amount or concentration in the extract to be able to prepare a therapeutically relevant dose, then the extract is considered part of the invention. The table below summarizes some of the relative efficacy data for three different forms of the cardiac glycoside oleandrin.

| DRUG | Human melanoma BRO cells ($IC_{50}$, μM) | Human pancreatic cancer PANC-1 cells ($IC_{50}$, μM) |
| --- | --- | --- |
| Pure Oleandrin | 0.017* | 0.01 |
| Hot water extract Comprising oleandrin and complex polysaccharides | 0.052 | 0.03 |
| Supercritical $CO_2$ extract comprising oleandrin and related cardiac glycosides | 0.007 | 0.004 |

*The $IC_{50}$ of tested compounds are presented as micromolar (μM) oleandrin equivalent concentrations in those extracts. That is, the data represent that concentration of oleandrin as free chemical or as part of an extract necessary to inhibit growth or proliferation of tumor cell growth compared to untreated cells by 50%.

As shown in the table above, the $IC_{50}$ value of the supercritical $CO_2$ extract is only 50% of that oleandrin alone in both Panc-1 and BRO cells, which suggests that the supercritical $CO_2$ extract of oleander is at least two-fold stronger (more potent) than oleandrin alone with respect to the inhibition of the growth of Panc-1 or BRO cells. In comparison, hot water extract is the least potent among three entities tested. The data demonstrate potent cytotoxicity against human tumor cell lines by oleandrin as well as the extracts with the relative potency occurring as follows: supercritical $CO_2$ extract>oleandrin>hot water extract. These data imply that the cytotoxicity of the supercritical CO₂ extract is probably due to the presence of at least one other pharmacologically active component in the SCF extract in addition to oleandrin and that the potency of the supercritical CO₂ extract is much greater (7.4 fold) than that of the hot water extract. The data clearly demonstrate the substantial improvement in efficacy of the SCF extract over the hot-water extract and even oleandrin alone. The improvement in efficacy exceeded the expected improvement that might have been obtained based solely upon the increased concentration of oleandrin in the SCF extract.

The invention also provides a method of inhibiting the proliferation of cancer or tumor cells by treatment of the cells with an effective of amount extract, such as SCF or water extract, of the invention.

The cardiac glycoside can be formulated in any suitable pharmaceutically acceptable dosage form. Parenteral, otic, ophthalmic, nasal, inhalable, buccal, sublingual, enteral, topical, oral, peroral, and injectable dosage forms are particularly useful. Particular dosage forms include a solid or liquid dosage forms. Exemplary suitable dosage forms include tablet, capsule, pill, caplet, troche, sache, and other such dosage forms known to the artisan of ordinary skill in the pharmaceutical sciences.

The amount of oleandrin incorporated in a unit dose of the invention will be at least one or more dosage forms and can be selected according to known principles of pharmacy. An effective amount or therapeutically relevant amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when, administered to a patient. The appreciable biological response may occur as a result of administration of single or multiple unit doses of an active substance. A unit dose may comprise one or more dosage forms. It will be understood that the specific dose level for any patient will depend upon a variety of factors including the indication being treated, severity of the indication, patient health, age, sex, weight, diet, pharmacological response, the specific dosage form employed, and other such factors.

The desired dose for oral administration is up to 5 dosage forms although as few as one and as many as ten dosage forms may be administered. Exemplary dosage forms contain 0.6 mg of the SCF extract per dosage form, for a total 0.6 to 60 mg (1 to 10 dose levels) per dose.

The cardiac glycoside can be present in a dosage form in an amount sufficient to provide a subject with an initial dose of oleandrin of 12 to 1200 ug, or more or less.

For use in treatment of mammals, the cardiac glycoside can be included in a dosage form. Some embodiments of the dosage form are not enteric coated and release their charge of cardiac glycoside within a period of 0.5 to 1 hours or less. Some embodiments of the dosage form are enteric coated and release their charge of cardiac downstream of the stomach, such as from the jejunum, ileum, small intestine, and/or large intestine (colon). Enterically coated dosage forms will release cardiac glycosides into the systemic circulation within 1-10 hr after oral administration.

Based on preliminary animal dosing data it is anticipated that 50 to 75% of an administered dose of oleander extract will be orally bioavailable therefore providing 0.25 to 0.4 mg, 0.1 to 50 mg, 0.1 to 40 mg, 0.2 to 40 mg, 0.2 to 30 mg, 0.2 to 20 mg, 0.2 to 10 mg, 0.2 to 5 mg, 0.2 to 2.5 mg, 0.2 to 2 mg, 0.2 to 1.5 mg, 0.2 to 1 mg, 0.2 to 0.8 mg, 0.2 to 0.7, or 0.25 to 0.5 mg of oleandrin per dosage form. Given an average blood volume in adult humans of 5 liters, the anticipated oleandrin plasma concentration will be in the range of 0.05 to 2 ng/ml, 0.005 to 10 ng/mL, 0.005 to 8 ng/mL, 0.01 to 7 ng/mL, 0.02 to 7 ng/mL, 0.03 to 6 ng/mL, 0.04 to 5 ng/mL, or 0.05 to 2.5 ng/mL. The recommended daily dose of oleandrin, present in the SCF extract, is generally about 0.25 to about 50 mg twice daily or about 0.9 to 5 mg twice daily or about every 12 hours. The dose can be about 0.5 to about 100 mg/day, about 1 to about 80 mg/day, about 1.5 to about 60 mg/day, about 1.8 to about 60 mg/day, about 1.8 to about 40 mg/day. The maximum tolerated dose can be about 100 mg/day, about 80 mg/day, about 60 mg/day, about 40 mg/day, about 38.4 mg/day or about 30 mg/day of oleander extract containing oleandrin and the minimum effective dose can be about 0.5 mg/day, about 1 mg/day, about 1.5 mg/day, about 1.8 mg/day, about 2 mg/day, or about 5 mg/day.

A kit or composition of the invention can include any excipients suitable for analytical or pharmaceutical use.

It should be noted that a compound herein might possess one or more functions in the formulation of the invention. For example, a compound might serve as both a surfactant and a water miscible solvent or as both a surfactant and a water immiscible solvent.

A liquid composition can comprise one or more pharmaceutically or analytically acceptable liquid carriers. The liquid carrier can be an aqueous, non-aqueous, polar, non-polar, and/or organic carrier. Liquid carriers include, by way of example and without limitation, a water miscible solvent, water immiscible solvent, water, buffer and mixtures thereof.

As used herein, the terms "water soluble solvent" or "water miscible solvent", which terms are used interchangeably, refer to an organic liquid which does not form a biphasic mixture with water or is sufficiently soluble in water to provide an aqueous solvent mixture containing at least five percent of solvent without separation of liquid phases. The solvent is suitable for administration to humans or animals. Exemplary water soluble solvents include, by way of example and without limitation, PEG (poly(ethylene glycol)), PEG 400 (poly(ethylene glycol having an approximate molecular weight of about 400), ethanol, acetone, alkanol, alcohol, ether, propylene glycol, glycerin, triacetin, poly(propylene glycol), PVP (poly(vinyl pyrrolidone)), dimethylsulfoxide, N,N-dimethylformamide, formamide, N,N-dimethylacetamide, pyridine, propanol, N-methylacetamide, butanol, soluphor (2-pyrrolidone), pharmasolve (N-methyl-2-pyrrolidone).

As used herein, the terms "water insoluble solvent" or "water immiscible solvent", which terms are used interchangeably, refer to an organic liquid which forms a biphasic mixture with water or provides a phase separation when the concentration of solvent in water exceeds five percent. The solvent is suitable for administration to humans or animals. Exemplary water insoluble solvents include, by way of example and without limitation, medium/long chain triglycerides, oil, castor oil, corn oil, vitamin E, vitamin E derivative, oleic acid, fatty acid, olive oil, softisan 645 (Diglyceryl Caprylate/Caprate/Stearate/Hydroxy stearate adipate), miglyol, captex (Captex 350: Glyceryl Tricaprylate/Caprate/Laurate triglyceride; Captex 355: Glyceryl Tricaprylate/Caprate triglyceride; Captex 355 EP/NF: Glyceryl Tricaprylate/Caprate medium chain triglyceride).

Suitable solvents are listed in the "International Conference on Harmonisation of Technical Requirements for Registration of Pharmaceuticals for Human Use (ICH) guidance for industry *Q3C Impurities: Residual Solvents*" (1997), which makes recommendations as to what amounts of residual solvents are considered safe in pharmaceuticals. Exemplary solvents are listed as class 2 or class 3 solvents. Class 3 solvents include, for example, acetic acid, acetone, anisole, 1-butanol, 2-butanol, butyl acetate, tert-butlymethyl ether, cumene, ethanol, ethyl ether, ethyl acetate, ethyl formate, formic acid, heptane, isobutyl acetate, isopropyl acetate, methyl acetate, methyl-1-butanol, methylethyl ketone, methylisobutyl ketone, 2-methyl-1-propanol, pentane, 1-pentanol, 1-propanol, 2-propanol, or propyl acetate.

Other materials that can be used as water immiscible solvents in the invention include: Captex 100: Propylene Glycol Dicaprate; Captex 200: Propylene Glycol Dicaprylate/Dicaprate; Captex 200 P: Propylene Glycol Dicaprylate/Dicaprate; Propylene Glycol Dicaprylocaprate; Captex 300: Glyceryl Tricaprylate/Caprate; Captex 300 EP/NF: Glyceryl Tricaprylate/Caprate Medium Chain Triglycerides; Captex 350: Glyceryl Tricaprylate/Caprate/Laurate; Captex 355: Glyceryl Tricaprylate/Caprate; Captex 355 EP/NF: Glyceryl Tricaprylate/Caprate Medium Chain Triglycerides; Captex 500: Triacetin; Captex 500 P: Triacetin (Pharmaceutical Grade); Captex 800: Propylene Glycol Di (2-Ethythexanoate); Captex 810 D: Glyceryl Tricaprylate/Caprate/Linoleate; Captex 1000: Glyceryl Tricaprate; Captex CA: Medium Chain Triglycerides; Captex MCT-170: Medium Chain Triglycerides; Capmul GMO: Glyceryl Monooleate; Capmul GMO-50 EP/NF: Glyceryl Monooleate; Capmul MCM: Medium Chain Mono- & Diglycerides; Capmul MCM C8: Glyceryl Monocaprylate; Capmul MCM C10: Glyceryl Monocaprate; Capmul PG-8: Propylene Glycol Monocaprylate; Capmul PG-12: Propylene Glycol Monolaurate; Caprol 10G100: Decaglycerol Decaoleate; Caprol 3GO: Triglycerol Monooleate; Caprol ET: Polygycerol Ester of Mixed Fatty Acids; Caprol MPGO: Hexaglycerol Dioleate; Caprol PGE 860: Decaglycerol Mono-, Dioleate.

As used herein, a "surfactant" refers to a compound that comprises polar or charged hydrophilic moieties as well as non-polar hydrophobic (lipophilic) moieties; i.e., a surfactant is amphiphilic. The term surfactant may refer to one or a mixture of compounds. A surfactant can be a solubilizing agent, an emulsifying agent or a dispersing agent. A surfactant can be hydrophilic or hydrophobic.

The hydrophilic surfactant can be any hydrophilic surfactant suitable for use in pharmaceutical compositions. Such surfactants can be anionic, cationic, zwitterionic or non-ionic, although non-ionic hydrophilic surfactants are presently preferred. As discussed above, these non-ionic hydrophilic surfactants will generally have HLB values greater than about 10. Mixtures of hydrophilic surfactants are also within the scope of the invention.

Similarly, the hydrophobic surfactant can be any hydrophobic surfactant suitable for use in pharmaceutical compositions. In general, suitable hydrophobic surfactants will have an HLB value less than about 10. Mixtures of hydrophobic surfactants are also within the scope of the invention.

Examples of additional suitable solubilizer include: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide); amides, such as 2-pyrrolidone, 2-piperidone, caprolactam, N-alkylpyrrolidone, N-hydroxyalkylpyrrolidone, N-alkylpiperidone, N-alkylcaprolactam, dimethylacetamide, and polyvinypyrrolidone; esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, valerolactone and isomers thereof, butyrolactone and isomers thereof; and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol nonoethyl ether (available from Gattefosse under the trade name Transcutol), and water. Mixtures of solubilizers are also within the scope of the invention.

Except as indicated, compounds mentioned herein are readily available from standard commercial sources.

The clear liquid composition is visually clear to the unaided eye, as it will contain less than 5%, less than 3% or less than 1% by wt. of suspended solids based upon the total weight of the composition.

Although not necessary, a composition or kit of the present invention may include a chelating agent, preservative, antioxidant, adsorbents, acidifying agent, alkalizing agent, antifoaming agent, buffering agent, colorant, electrolyte, salt, stabilizer, tonicity modifier, diluent, other pharmaceutical excipient, or a combination thereof.

As used herein, the term "antioxidant" is intended to mean an agent that inhibits oxidation and is thus used to prevent the deterioration of preparations by the oxidative process. Such compounds include, by way of example and without limitation, ascorbic acid, ascorbic palmitate, Vitamin E, Vitamin E derivative, butylated hydroxyanisole, butylated hydroxytoluene, hypophosphorous acid, monothioglycerol, propyl gallate, sodium ascorbate, sodium bisulfite, sodium formaldehyde sulfoxylate, sodium metalbisulfite and other such materials known to those of ordinary skill in the art.

As used herein, the term chelating agent is intended to mean a compound that chelates metal ions in solution. Exemplary chelating agents include EDTA (tetrasodium ethylenediaminetetraacetate), DTPA (pentasodium diethylenetriaminepentaacetate), HEDTA (trisodium salt of N-(hydroxyethyl)-ethylenediaminetriacetic acid), NTA (trisodium nitrilotriacetate), disodium ethanoldiglycine ($Na_2EDG$), sodium diethanolglycine (DEGNa), citric acid, and other compounds known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide an alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium. Such compounds include, by way of example and without limitation, acetic acid, amino acid, citric acid, fumaric acid and other alpha hydroxy acids, hydrochloric acid, ascorbic acid, and nitric acid and others known to those of ordinary skill in the art.

As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

As used herein, the term "buffering agent" is intended to mean a compound used to resist a change in pH upon dilution or addition of acid or alkali. Such compounds include, by way of example and without limitation, potassium metaphosphate, potassium phosphate, monobasic sodium acetate and sodium citrate anhydrous and dehydrate and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl, or butyl parabens and others known to those of ordinary skill in the art.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, FD&C Green No. 5, FD&C Orange No. 5, FD&C Red No. 8, caramel, and iron oxide (black, red, yellow), other FD&C dyes and natural coloring agents such as grape skin extract, beet red powder, beta-carotene, annato, carmine, turmeric, paprika, combinations thereof and other such materials known to those of ordinary skill in the art.

As used herein, the term "stabilizer" is intended to mean a compound used to stabilize an active agent against physical, chemical, or biochemical processes that would otherwise reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those or ordinary skill in the art.

Examples 3 and 6 describe an exemplary capsule dosage form. Example 12 describes an exemplary tablet dosage form.

The composition of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The composition can also include alcohol such as ethanol, isopropanol, hexadecyl alcohol, glycerol and propylene glycol; glycerol ketals such as 2,2-dimethyl-1,3-dioxolane-4-methanol; ethers such as poly (ethylene glycol) 450; petroleum hydrocarbons such as mineral oil and petrolatum; water; a pharmaceutically suitable surfactant, suspending agent or emulsifying agent; or mixtures thereof.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

One or more of the components of the formulation can be present in its free base or pharmaceutically or analytically acceptable salt form. As used herein, "pharmaceutically or analytically acceptable salt" refers to a compound that has been modified by reacting it with an acid as needed to form an ionically bound pair. Examples of acceptable salts include conventional non-toxic salts formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Lists of other suitable salts are found in *Remington's Pharmaceutical Sciences*, 17$^{th}$. ed., Mack Publishing Company, Easton, Pa., 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

Oleandrin and MTT are purchased from Sigma Chemical Co. (St. Louis, Mo.). BODIPY-oleandrin, Mito-Tracker Red CM-H$_2$XRos, calcein acetoxymethyl (CAM) ester and 4'-6-diamidino-2-phenylindole (DAPI) are obtained from Molecular Probes-Invitrogen Corporation (Carlsbad, Calif.). Anti-β-actin antibody is also purchased from Sigma.

Human pancreatic cancer cells: Panc-1, BxPC3, MiaPaca; human colon cancer cell lines: CaCO-2, DOD-1, HCT-116, HT29, RKO and LST174; rodent melanoma B16 cells; human breast cancer cells: SUM149, MCF-7 and MDA231; human oral cancer cells: SCC9 and CAL-27; human ovarian cancer ES3, TOV1120 and SKOV cells and human non-small cell lung cancer A549 and H1299 cells are obtained from the American Type Culture Collection (Manassas, Va.) and maintained in a humidified atmosphere containing 5% $CO_2$ at 37° C. Human melanoma BRO cells were a kind gift from the Stehlin Foundation (Houston, Tex.). Cell lines derived from different epithelial origins are routinely cultured in tissue culture medium (Invitrogen Corp., Grand Island, N.Y.) (Table 1) supplemented with 10% heat inactivated fetal bovine serum (FBS) Hyclone Laboratories Inc., Logan, Utah), 50 IU/ml penicillin and 50 µg/ml streptomycin, and 2 mM L-glutamine from GIBCO (Invitrogen).

Example 1

Supercritical Fluid Extraction of Powdered Oleander Leaves

Method A. with Carbon Dioxide.

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.94 kg.

The starting material was combined with pure $CO_2$ at a pressure of 300 bar (30 MPa, 4351 psi) and a temperature of 50° C. (122° F.) in an extractor device. A total of 197 kg of $CO_2$ was used, to give a solvent to raw material ratio of 50:1. The mixture of $CO_2$ and raw material was then passed through a separator device, which changed the pressure and temperature of the mixture and separated the extract from the carbon dioxide.

The extract (65 g) was obtained as a brownish, sticky, viscous material having a nice fragrance. The color was likely caused by chlorophyll. For an exact yield determination, the tubes and separator were rinsed out with acetone and the acetone was evaporated to give an addition 9 g of extract. The total extract amount was 74 g. Based on the weight of the starting material, the yield of the extract was 1.88%. The content of oleandrin in the extract was calculated using high pressure liquid chromatography and mass spectrometry to be 560.1 mg, or a yield of 0.76%.

Method B. with Mixture of Carbon Dioxide and Ethanol

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.85 kg.

The starting material was combined with pure $CO_2$ and 5% ethanol as a modifier at a pressure of 280 bar (28 MPa, 4061 psi) and a temperature of 50° C. (122° F.) in an extractor device. A total of 160 kg of $CO_2$ and 8 kg ethanol was used, to give a solvent to raw material ratio of 43.6 to 1. The mixture of $CO_2$, ethanol, and raw material was then passed through a separator device, which changed the pressure and temperature of the mixture and separated the extract from the carbon dioxide.

The extract (207 g) was obtained after the removal of ethanol as a dark green, sticky, viscous mass obviously containing some chlorophyll. Based on the weight of the starting material, the yield of the extract was 5.38%. The content of oleandrin in the extract was calculated using high pressure liquid chromatography and mass spectrometry to be 1.89 g, or a yield of 2.1%.

Example 2

Hot-Water Extraction of Powdered Oleander Leaves

Hot water extraction is typically used to extract oleandrin and other active components from oleander leaves. Examples of hot water extraction processes can be found in U.S. Pat. No. 5,135,745 and U.S. Pat. No. 5,869,060.

A hot water extraction was carried out using 5 g of powdered oleander leaves. Ten volumes of boiling water (by weight of the oleander starting material) were added to the powdered oleander leaves and the mixture was stirred constantly for 6 hours. The mixture was then filtered and the leaf residue was collected and extracted again under the same conditions. The filtrates were combined and lyophilized. The appearance of the extract was brown. The dried extract material weighed about 1.44 g. 34.21 mg of the extract material was dissolved in water and subjected to oleandrin content analysis using high pressure liquid chromatography and mass spectrometry. The amount of oleandrin was determined to be 3.68 mg. The oleandrin yield, based on the amount of extract, was calculated to be 0.26%. The table below shows a comparison between the oleandrin yields for the two supercritical carbon dioxide extractions of Example 1 and the hot water extraction.

Comparison of Yields

| Extraction Medium | Oleandrin yield based on total extract weight |
| --- | --- |
| Supercritical Carbon Dioxide: Example 1, Method A | 0.76% |
| Supercritical Carbon Dioxide: Example 1, Method B | 2.1% |
| Hot Water Extraction: Example 2 | 0.26% |

Example 3

Cell Lines

Human pancreatic cancer cells: Panc-1, BxPC3, MiaPaca; human colon cancer cell lines: CaCO-2, DOD-1, HCT-116, HT29, RKO and LST174; rodent melanoma B16 cells; human breast cancer cells: SUM149, MCF-7 and MDA231; human oral cancer cells: SCC9 and CAL-27; human ovarian cancer ES3, TOV1120 and SKOV cells and human non-small cell lung cancer A549 and H1299 cells were obtained from the American Type Culture Collection (Manassas, Va.) and maintained in a humidified atmosphere containing 5% $CO_2$ at 37° C. Human melanoma BRO cells were a kind gift from the Stehlin Foundation (Houston, Tex.). Cell lines derived from different epithelial origins were routinely cultured in tissue culture medium (Invitrogen Corp., Grand Island, N.Y.) (Table 1) supplemented with 10% heat inactivated fetal bovine serum (FBS) Hyclone Laboratories Inc., Logan, Utah), 50 IU/ml penicillin and 50 µg/ml streptomycin, and 2 mM L-glutamine from GIBCO (Invitrogen).

Example 4

In Vitro Determination of Cytotoxicity

Cells were grown in their relevant media as indicated in the table below at a density of $1 \times 10^4$ cells/well. After a 24 hr incubation period, cells were treated with various concentrations of oleandrin (1 to 500 nM). After an additional 72 hr, inhibition of cellular proliferation was assessed by MTT assay (23). Absorbance was read at a wavelength of 570 nm and a reference wavelength of 650 nm using a V-Max Micro-plate Reader by Molecular Devices, Inc. (Sunnyvale, Calif.). The relative extent of inhibition of cell proliferation due to the presence of a given concentration of oleander extract or other plant extract containing a cardiac glycoside compound(s) can be derived by comparing treated to non-treated cell numbers after a set period of time allowing for cell growth (e.g. 24-72 hr).

| Name of cells | Phenotype description | Cell culture medium |
|---|---|---|
| PANC-1 | Human pancreatic carcinoma | DMEM/10% FBS |
| BXPC3 | Human pancreatic adenocarcinoma | RPMI 164/10% FBS/sodium pyruvate (NaP) |
| MiaPaca | Human pancreatic adenocarcinoma | DMEM/10% FBS/ 2% Equine serum |
| MDA 231 | Breast cancer | DMEM/10% FBS |
| SUM 149 | Breast cancer | F12/5% FBS/ HEPES/insulin/hydrocortisone |
| CaCO2 | Colon carcinoma | RPMI 1640/10% FBS |
| DOD-1 | Colon carcinoma | RPMI 1640/10% FBS |
| HCT 116 | Colon carcinoma | RPMI 1640/10% FBS |
| HT 29 | Colon carcinoma | RPMI 1640/10% FBS |
| LIS-174t | Colon carcinoma | MEM/10% FBS/NaP/NEAA |
| BRO | Acute lymphoblastic leukemia | MEM/10% FBS/NaP |
| SCC-9 | Mouth squamous cell carcinoma | DMEM/10% FBS |
| CAL27 | Mouth squamous cell carcinoma | DMEM/10% FBS |
| MCF-7 | Breast cancer | MEM/10% FBS/ insulin/hydrocortisone/EGF |

Note:
DMEM = Dulbecco's Modified Eagle's Medium;
MEM = Minimum Essential Medium;
FBS = Fetal bovine serum;
NEAA = non-essential amino acids;
EGF = Epidermal growth factor.

Example 5

Determination of Cellular Uptake of Cardiac Glycoside

Uptake of oleandrin and ouabain in Panc-1 (highest ratio of α3:α1 isoforms) cells and BxPC3 cells (lower ratio of α3:α1) was determined after treatment with BODYPI-oleandrin, a fluorescent analog of oleandrin, by fluorescence microscopy. Cells in 96-well plates were treated with 0, 5, 20, and 50 nM oleandrin for 2 h or 24 h. Treatments were performed in 0.5% fetal bovine calf serum in DMEM/F12 medium. Cells were simultaneously incubated with MitoTracker Red CM-$H_2$XRos (1 μM), and DAPI (1 ng/ml), a selective nuclear dye (Molecular Probes). Nuclear morphology, DNA and mitochondria dye uptake were assessed by fluorescence microscopy using an Olympus IX-70 inverted microscope. Image acquisition was achieved using a Quantix charged coupled device camera and IP Labs software (Scanalytics, Inc., Fairfax, Va.). Alteration of oleandrin uptake in wild type and Panc-1 cells transfected with α3 siRNA was determined in cells cultured on laminin coated coverslips and treated with BODIBY-oleandrin for 1 hr.

Example 6

Determination of Na, K-ATP as α3 and α1 Isoform Expression

Cells were washed with cold PBS and scraped free in the presence of lysis buffer (20 mM MOPS, 2 mM EGTA, 5 mM EDTA, 30 mM NaF, 40 mM β-glycerophosphate, 20 mM sodium pyruvate, 0.5% Triton X-100, and 1 mM sodium orthovanadate with protease inhibitor cocktail). Cell lysates were then sonicated on ice for 3 min, incubated for an additional 10 min at 4° C. prior to centrifugation at 14,000×g (10 min at 4° C.). Protein levels were quantified via the BioRad Dc protein assay (BioRad, Inc., Hercules, Calif.). Equal levels of protein (50 μg) were applied to precast gels (BioRad) and then transferred onto polyvinylidene diflouride membranes, according to standard methods. Following a 1- to 2-hr incubation period in 5% nonfat dry milk blocking buffer prepared in Tris-buffered saline with 0.1% Tween 20, membranes were probed with primary antibodies to α3 (Affinity Bioreagents, Golden, Colo.) and α1 (Upstate, Lake Placid, N.Y.) isoforms diluted 1:2,000 in blocking buffer. Protein bands were visualized via chemluminesence using the ECL+detection kit and hyper-film (Amersham Biosciences, Piscataway, N.J.). Equal loading of samples was illustrated by Western blotting for the presence of β-actin. Protein bands were quantified using Alpha DigiDoc 1000 software (Alpha Innotech Corp., San Leandro, Calif.).

Example 7

Treatment of Skin Related Diseases Such as Cancers Including but not Limited to Prevention of Treatment of Melanoma, Basal Cell Carcinoma, and Squamous Cell Carcinoma as Well as Noncancerous Inflammatory Skin Diseases Including but not Limited to Actinic Keratosis, Psoriasis, and Eczema The SCF extract is administered to a subject suffering from malignant or nonmalignant proliferative skin diseases such as those cited above. The SCF extract is administered as a cream or ointment or contained within a dermal patch containing 0.01 mg to 10 mg of SCF extract per unit dose. The subject is administered a unit dose up to three times daily for a period of 1 to 14 days or until the skin diseases is in remission. It is expected that such treatment will significantly lessen or eliminate the inflammation and malignant processes leading to a progression of the disease. The subject should experience a reduction in the severity of the dermal lesion(s) and the eventual resolution of the dermatologic disease itself. Malignant diseases should be expected to be reduced in rate of growth or inhibited from increase in severity of the disease. Actual regression of established malignant lesions may be expected.

Example 8

Prevention of Skin Related Diseases Such as Skin Cancers

The SCF extract is administered to a subject suffering from a predisposition to formation of skin cancer such as those frequently exposed to ultraviolet light (from sunlight) or carcinogens from chemicals. The SCF extract is administered as a cream or ointment or contained within a dermal patch containing 0.01 to 10 mg of SCF extract per unit dose. The subject is administered a unit dose up to three times daily every time exposure to a carcinogen promoting event is anticipated (exposure to sunlight). Such administration could, for example, be made as a sunscreen for blocking sunlight UV exposure and SCF extract for prevention of tumor induction in dermal tissue. It would be expected that such a use of the SCE in a dermal product would block formation and/or promotion of malignant skin disease or nonmalignant skin disorders where proliferation leads to a worsening of the disease process (e.g. acktinic keratosis, psoriasis and/or eczema).

Example 9

Treatment of Solid Tumors in Humans or Other Vertebrate Animals

SCF extract of plants or animals containing cardiac glycosides can be used to treat cancers of the rectum, anus, colorectal tissues, head and neck tissues, esophageal tissue, lung (both non small cell and small cell carcinomas), breast, stomach, pancreas, prostate, liver, kidney, bladder, ureter, ovarian tissue, carcinoid tumors, sarcomas of bone, mesothelioma, and neoplasms of the central nervous system.

The SCF extract is administered to a subject suffering from solid malignant diseases such as those mentioned above. The SCF extract is administered as an oral dosage form containing 1 to 50 mg of SCF extract per unit dose. The subject is administered a unit dose up to twice daily times daily for a period of 28 days/cycle of treatment. Up to three cycles of treatment may be required. The subject should experience tumor growth to either slow in rate of proliferation or to regress. Completion resolution of the tumor may occur. The therapy with SCF extract may be used as a sole agent or combined with cytotoxic chemotherapy or radiation treatment or may be combined with appropriate immunotherapy without causing undue interference with the desired antitumor effect of conventional therapy.

Example 10

Comparison of Cytotoxicity of Hot Water Extract of *Nerium oleander* to an SCF Extract Made Using Supercritical $CO_2$ in Two Human Tumor Cell Lines The cytotoxic potential of both extracts are compared directly with that of oleandrin. The samples contained the same amounts of oleandrin even though their concentration of oleandrin differed due to the concentration of oleandrin present in the extracts.

BRO (human melanoma) and Panc-1 (human pancreatic cancer) cells ($8 \times 10^3$/well) were plated in a 96 well plate and allowed to attach overnight. Drug or extracts were then added to the cells. After 72 hr of incubation, relative cell proliferation (relative to control untreated cells) was assessed by crystal violet staining method.

Example 11

HPLC Analysis of Solutions Containing Oleandrin

Samples (oleandrin standard, SCF extract and hot-water extract) were analyzed on HPLC (Waters) using the following conditions: Symmetry C18 column (5.0 µm, 150×4.6 mm I.D.; Waters); Mobile phase of MeOH:water=54: 46 (v/v) and flow rate at 1.0 ml/min. Detection wavelength was set at 217 nm. The samples were prepared by dissolving the compound or extract in a fixed amount of HPLC solvent to achieve an approximate target concentration of oleandrin.

Example 12

Evaluation of Anti-Viral Activity of an SCF Extract

The test consists of determining the relative ability of oleander extract or a positive control (AZT) to inhibit proliferation of the ROJO strain of HIV-1 in human peripheral blood mononuclear cells (PBMCs). Infected cells are exposed to the drug or extract for 48 hr. The test is used to determine the $IC_{50}$ of oleander extract (that concentration of extract producing a 50% inhibition of viral proliferation) versus that concentration of extract capable of killing the human PBMC. This is, in effect, a determination of the therapeutic index of the extract. This is essentially a determination of whether or not the extract can kill HIV-1 without killing the PBMC cell itself.

One should observe an $IC_{50}$ against viral proliferation of about 5.0 ug/ml or less while the concentration required to kill cells should not have been reached even at concentrations as high as 100 ug/ml. The data obtained suggest that oleander extract should be useful in terms of inhibiting HIV-1 viral proliferation or infectivity of virus harbored within PBMC cells.

Example 13

Transfection of Panc-1 Cells with α3 siRNA

Panc-1 cells were plated in 6 and 48 well plates and allowed to attach overnight. Transient transfection of α3 siRNA molecules was carried out using siPORT™ Amine Transfection Agent (Ambion Austin, Tex.) and 0.4 µM α3 silencing RNA (Santa Cruz Biotech.) following the manufacture's instructions. Twenty-four hr after transfection, cells were treated with 10 to 50 nM oleandrin for 48 hr. Protein was collected from the 6 well plates for Western blot analysis and cell viability assessment was carried out by Calcien AM staining.

Example 14

Determination of α3 and α1 Expression in Normal and Colon Biopsy Tissues

Flash frozen normal colon mucosa and tumor tissue biopsys were obtained and were pulverized with use of a liquid nitrogen cooled mortar. Samples were exposed to lysis buffer as indicated above. Lysates were then sonicated on ice for 3 min., incubated at 4° C. for 10 min. and centrifuged at 14,000 rpm (10 min. at 4° C.) followed by Western blotting analysis of α3 and α1 isoforms of the α-subunit as described previously.

Example 15

Statistical Analysis

Student's t test was used to determine the statistical differences between various experimental groups; a value of $P<0.05$ was considered to be significant.

Example 16

Determination of the Sensitivity of α3 Antibody

To compare the sensitivity of different α3 antibodies, equal amounts of the same lysates of positive and negative control samples were loaded onto 3 precast gels (BioRad, Inc., Hercules, Calif.) and then transferred to polyvinylidene diflouride membranes, according to standard methods. Following a 1-2 hr incubation in 5% nonfat dry milk blocking buffer prepared in tris-buffered saline with 0.1% tween 20 (TBS-T), membranes were probed with α3 antibodies from Sigma (St Luoise, Mo.), from Affinity Bioreagents (Golden, Colo.) and from Novus (Littleton, Colo.), each at a 1:2000 dilution in blocking buffer. Protein bands were visualized via chemiluminesence, using the Chemiglow West detection kit and Alpha Imager (Alpha InnotechCorp., San Leandro, Calif.). Protein bands were quantified and compared between the three antibodies, using Alpha DigiDoc 1000 software (Alpha Innotech Corp., San Leandro, Calif.). Equal loading of samples was illustrated by Western blotting for β-Actin. The data indicate that sensitivity of each one of the selected antibodies to α3 is substantially the same.

| Source of α3 monoclonal antibodies | Average density* |
| --- | --- |
| Affinity Bioreagents | 45174 |
| Novus | 41110 |
| Sigma | 44572 |

*Average density was calculated based on the absolute density of each band divided by the defined area which is quantified by Alpha DigiDoc 1000.

Example 17

Kit for Conducting Prognostic Assay

This kit can be used according to the method of the invention to conduct a prognostic assay using a Western blot technique, such as detailed in Example 18.

1. Lysis composition

|  | 5 ml | From Stock solution concentration of: |
| --- | --- | --- |
| 20 mM Tris HCL pH 8.0 | 100 ul | 1M |
| 137 mM NaCl | 685 ul | 1M |
| 10% Glycerol | 500 ul |  |
| 5 mM EDTA | 25 ul | 1M |
| 1% NP-40 | 50 ul |  |
| Protease Inhibitor cocktail (Sigma, Cat# P8340) | 50 ul |  |
| 1 mM Na Orthovanadate | 50 ul | 100 mM |
| $H_2O$ | 3540 ul |  |

2. Primary antibodies: (1:2000 in blocking solution)
Alpha 3 (Affinity Bioreagents Cat #MA3-915)
Alpha 1 (Upstate Cat #05-369)
3. Secondary antibody: Goat anti-mouse IgG HRP (Santa Cruz Cat #sc-2005)
4. Gel/Membrane Prep:
7.5-10% Gels (BioRad Precast)
BioRad Laemmli sample buffer (Cat #161-0737)
Molecular weight marker (Cat #161-0318)
Running buffer (BioRad 10× Tris/glycine/SDS) (Cat #161-0732)
Membranes (Biorad PVDF)

| Transfer buffer: | |
| --- | --- |
| 3.03 g | Tris (final concentration - 25 mM) |
| 14.4 g | Glycine (final concentration - 0.192 mM) |
| 200 ml | Methanol (20%) |
| up to 1 L | $H_2O$ |

5. Blocking solution: 5% milk in TBS (20 mM Tris HCl, 150 mM NaCl)
6. Wash buffer: TBS-T (20 mM Tris HCl, 150 mM NaCl, 0.05% Tween-20)
8. Positive control cells: cell lysate of human pancreatic cancer Panc-1 cells
9. Negative control cells: Mouse melanoma B16 cells
10. Brochure including the detailed protocol for western blotting analysis of the isoforms of the α-subunit.

Example 18

Preparing Samples of Cellular Tissue

Method A. From Cell Pellet
Obtain a cell pellet containing 2 to 4 million cells. Rinse with physiologic balanced solution (PBS) to remove media. Add 100 ul lysis buffer. Keep cold (over ice) at all times. Continue to sonication step in Example 18.
Method B. From Cells on Plate
Grow 1.2 to 1.5 million cells on a 100 mm tissue culture plates for 24 hrs. Carefully decant and discard cell growth media. Rinse plate 2 times with 1 ml PBS. Add 100 ul lysis buffer, scrape cells from plate, and collect in tubes. Keep cold (over ice) at all times. Continue to sonication step in Example 18.
Method C. From Tissue
Grind frozen tissue. Place ground tissue in tubes. Add 100 μl of cold lysis buffer to a minimum of 5 mg of ground tissue. Keep cold (over ice) at all times. Continue to sonication step in Example 18.

Example 19

Determining Content of Isoforms of the α-Subunit in Sample by Western Blot

The following procedure is merely one way in which the method of the invention can be employed to detect and quantify the content of the isoforms of the α subunit of Na, K-ATPase in a sample. The order of the steps can be modified as needed.
Western Blot Analysis
1. Sonicate cell lysate while cooling, such as with an ice-chilled bath.
2. Spin lysate @ 4° C. for 10 min at 14,000 rpm.
3. Collect the supernatant—keep on ice at all times.
4. Determine the protein levels by protein assay. (See BioRad® Protein Assay Kit directions)
5. Prepare samples for loading on gel based on protein assay (50 μg of protein per well).
   a. Prepare a positive and negative control lysate along with the samples.
      i. Positive control: Panc-1 protein lysate
      ii. Negative control: Panc-2 or B16 protein lysate
   b. Add laemmli sample buffer (LSB) to samples and controls (see LSB directions)
   c. Heat samples and controls @ 95 C for 5 min.
   d. Spin down samples 6. Load gels.
7. Run gel at 200 volts until the dye runs off the bottom of the gel.
8. Transfer at 100 volts for 1-2 hours.
9. Block membrane 30 min to 1hr in blocking buffer@ RT.
10. Incubate membrane overnight at 4° C.
11. Wash membrane with wash buffer:
    3 quick washes, 1-15 min wash, 2-10 min washes
12. Incubate membrane for 45 min to 1 hr in II° antibody at RT.
13. Wash membrane with wash buffer:
    3 quick washes, 1-15 min wash, 2-10 min washes
14. Incubate membrane for 5 min in ECL+(Amersham Cat #RPN2132).
15. Expose membrane to film (Amersham Cat #RPN3114k) and develop on film developer machine.
16. Take a picture of the exposed film with the Alpha Imager, using Alpha Digi Doc software (or your current imager).
17. Using the Spot Denso application of the Analysis tools in Alpha Digi Doc, select the corresponding bands of the Alpha 1 and Alpha 3 images.
18. Obtain the Integrated Density Value (IDV) for each band.
19. Calculate the ratio of α3 isoform to α1 isoform.

Example 20

RT-PCR Method for Determination of mRNA for Na,K-ATPase Specific Alpha Subunits

The RNA STAT-60 reagent (Tel-Test, Inc., Friendswood, Tex.) was used to extract the total RNA, which was treated with DNase I prior to use in a reverse transcriptase-polymerase chain reaction (RT-PCR) analysis. One microgram of RNA was reverse transcribed with mouse mammary tumor virus RT (Life Technologies, Inc., Rockville, Md.). α3-371 bp sequences were amplified by primer set α3-NKA3VSAS-2-F 5'-NNNNNNNNNN-3' (forward) (SEQ ID NO. 3) and —R 5'-NNNNNNNN-3' (reverse). These sets and additional primer sets were designed and verified using Oligo 6.7 Molecular Biology Insights (Cascade, Colo.). Primer pairs (5'-CAGCTCTGGAGAACTGCTG-3' (SEQ ID NO. 1); 5'-GTGTACTCAGTCTCCACAGA-3' (SEQ ID NO. 2)) were used in RT-PCR analysis to detect GAPDH mRNA.

Example 21

Clinical Evaluation of the Combination of a Cardiac Glycoside-Containing Extract with Other Anticancer Drugs for the Treatment of Metastatic Pancreatic Gastrinoma The following is a case history wherein a patient suffering from metastatic pancreatic gastrinoma was treated with a cardiac glycoside-containing extract.

A sixty three year old male presented to clinic at M. D. Anderson Cancer Center on Aug. 30, 2002 with suspected pancreatic disease. CT Scan revealed mass on tail of pancreas. On Sep. 17, 2002 patient began to self-administer an experimental drug containing cardiac glycosides, principally oleandrin. On Oct. 9, 2002 patient was diagnosed with well-differentiated islet cell tumor of the pancreas. Patient was recommended for eight cycles of chemotherapy of Adriamycin, streptozocin, and 5-FU followed by three cycles of streptozocin and 5-FU. On Nov. 13, 2002, patient began recommended therapy while continuing to self-administer the drug containing oleandrin. On Jul. 23, 2003, patient concluded the recommended regimen of chemotherapy. No change was noted in his original diagnosis. Patient received no chemotherapy subsequent to Jul. 23, 2003. Patient continued to self-administer the extract containing cardiac glycosides subsequent to the conclusion of the chemotherapy regimen. Patient is described as late as Feb. 16, 2007 as having radiologically stable disease. Patient continues to self-administer the extract containing cardiac glycoside, such as oleandrin, and is asymptomatic and reports 100% on a Karnofsky scale.

Example 22

Clinical Evaluation of a Cardiac Glycoside-Containing Extract for the Treatment of Adenocarcinoma A 35-year-old man experienced pain and bloating in his abdomen following eating regular meals. He presented to a private clinic, and spiral abdomen computer aided tomography (CAT) scan was performed. Among the conclusions was volumetric increase of the pancreas head, heterogeneity in the density of parenchyma, and multiple lymphadenopathies at the anterior site of the pancreas head. Magnetic resonance imaging (MM) examination on confirmed these findings. Ultrasound aided thin needle aspiration biopsy was performed on the same day. Ultrasound examination demonstrated a tumoral mass of 39×33 mm in the pancreas head. Histopathological examination of the biopsy specimen revealed the diagnosis as adenocarcinoma. A course of chemotherapy was recommended, but the patient declined.

A month later, the patient began a self-administered botanical extract therapy that contained very small quantities of oleandrin. Upper abdomen MR images obtained within a month demonstrated a contrast retaining lesion of 35×25 mm on the head of the pancreas. Numerous lymphadenopathies, of which the largest one was 5 mm, were also revealed at the anterior site of the pancreas head and the stomach antrum posterior site.

MM images obtained three months later showed that the tumor in the pancreas head measured 30×25 mm. Dosage of the extract containing small amounts of oleandrin was increased at this time. A bone scintigraphy was performed three weeks later. It was unremarkable for metastatic disease. Upper and lower abdominal MRI images obtained seven weeks later demonstrated that the tumoral mass in the head of pancreas and all the lymphadenopathies were indicative of remission. An upper and lower abdominal MRI obtained two months later, was unremarkable for pancreatic adenocarcinoma and/or lymphadenopathies. A follow up upper and lower abdominal MRI was performed four months later. It continued to be unremarkable for pancreatic adenocarcinoma and metastatic disease.

As of March 2007, the patient continues in remission.

Example 23

Culture of Cancer and Tumor Cells

The following procedure can be modified as needed to optimize the culture of specific cancer or tumor cells. Panc-1 human pancreatic cancer cells were purchased from the American Type Culture Collection (Manassas, Va.). Cells were cultured in DMEM media supplemented with 10-15% fetal bovine serum (Invitrogen, Carlsbad, Calif.), 100 U/ml of penicillin (Invitrogen), and 2.5 ug/ml of antimycotic (Fungizone; Invitrogen) at 37° C. in 5% $CO_2$. Relative inhibition of cell proliferation by oleandrin and Adriamycin was determined after 72 hr of continuous drug exposure of a series of concentrations of each drug. The MTT assay was used as previously described (Mosmann, 1983) to assess cell growth relative to untreated Panc-1 cell proliferation. Cells were exposed to no treatment (controls), oleandrin or Adriamycin for 72 prior to assessment of cell growth.

Example 24

Cell Staining

The following procedure was used to stain cells with acridine orange.

Cells were stained with 1 ug/ml acridine orange for 15 min. at 37° C. Cells were washed with PBS, trypsinized from the plates, collected in PBS with FBS, and analyzed via flow cytometry.

Example 25

Cell Cycle Analysis

The following procedure was used to determine cell cycle.

Panc-1 cells were treated with oleandrin (0, 20 and 40 uM) for 72 hr, trypsinized, fixed with 4° C. 70% ethanol, stained with propidium iodide by using a cellular DNA flow cytometric analysis reagent set (Roche), and then analyzed for DNA content by FACScan (Becton Dickinson, San Jose, Calif.). Data were analyzed by Cell Quest software (Becton Dickinson). At least 100,000 cells were analyzed for each sample.

Example 26

Clinical Evaluation of a Cardiac Glycoside-Containing Extract for the Treatment of Non-Small Cell Lung Cancer An eighty one year-old male was diagnosed with non small cell lung cancer of the left upper lobe. Patient was recommended for radiation therapy followed by a course of chemotherapy. Seven weeks later, the patient began the radiation therapy and completed therapy in 24 days. The patient then commenced a regimen of five chemotherapeutic within six days and completed them eight months later. Twenty seven days prior to completion, he presented to clinic for restaging of prior diagnosis of non small cell lung cancer of the left upper lobe. A whole body PET scan was performed and was conclusive for a large area of abnormal hyper metabolic activity involving the left upper lobe consistent with patient's known malignancy. Additionally, subtle areas of hyper metabolic activity involving the right hilum and anterior mediastinum likely reflected nodal involvement. A CT scan of the chest confirmed a 5-cm soft-tissue density in the upper left lobe. A subsequent chemotherapeutic regimen was initiated. Within one month, chemotherapy was discontinued due to intolerance by patient. A week later, a CT scan of the chest was performed for comparison. There was an approximately 4 cm soft-tissue mass in the posterior segment of the left upper lobe. There was an interval decrease in overall bulk of left upper lobe mass. Within five weeks, the patient began self-administration of a botanical extract containing oleandrin. After three months, a follow-up chest PA & Lateral was compared with the prior scan, and the tumor mass density in the left upper lobe was unchanged. A year later a chest PA & Lateral was compared to the findings of a scan of three months prior, and it was determined that the tumor mass density measuring about 4 cm in the left upper lobe above the hilum was unchanged.

The patient continued to self-administer the botanical extract containing oleandrin. Within four months, a CT scan of chest with IV contrast was conducted. An approximately 20% decrease in size of central mass of upper left lobe was observed. At present date, the patient continues to self-administer the botanical extract containing oleandrin and reports high Karnofsky score. Clinical data suggests that the botanical extract has therapeutic benefit, since the changes in the size of the central mass occurred many months after patient's last chemotherapy.

Example 27

Determining Content of Isoforms of the α-Subunit in Ssample by Immunohistochemical Staining The following procedure is merely an alternative way in which the method of the invention can be employed to detect and quantify the content of the isoforms of the α subunit of Na, K-ATPase in a sample. The order of the steps can be modified as needed. The materials used in this assay can be obtained from Vector Laboratories (Burlingame, Calif. or Peterborough, England).

Immunohistochemical Analysis

Fresh frozen sections of human tissues were used. Sections were deparaffinized with 3 changes of xylene (5 min each), rehydrated in a descending ethanol series (99%×2, 90%×2 for 5 min each), and rinsed well in distilled water. Heat mediated antigen retrieval methodology was completed by incubation of sections for 3×5 min in a boiling solution of Vector antigen unmasking solution (Vector-AMS), high pH (Vector Laboratories Catalog #H-3301).

Following antigen retrieval, sections were washed in 50 mM Tris HCl, 300 mM NaCl, 0.1%, pH 7.6 (TBS) for 2×5 min. Endogenous peroxide activity was quenched by incubating the sections for 20 min in 0.3% 9 v/v) hydrogen peroxide in methanol, followed by washing in TBS for 10 min.

Sections were incubated for 1 hour with anti-Na, K-ATPase α3 subunit isoform antibody (Sigma-Aldrich Cat #A273) diluted in 2.5% (v/v) normal horse serum (2.5% NHS) in TBS at 4 ug/ml. The negative control sections were incubated with a non-immune mouse IgG1 antibody (Biostat Diagnostics, Cat #093101) at 4 ug/ml or in 2.5% NHS ('no primary' control).

Following washing in TBS for 2×5 min, the sections were incubated with Vector ImmPress™ universal antibody reagent (a mixture of anti-rabbit IgG and anti-mouse IgG reagents; Vector Laboratories Ltd., Cat #MP-7500) for 30 min. The sections were then washed for 2×5 min and incubated with diaminobenzidine (DAB) substrate, with monitoring until a suitable level of staining had developed. The chromagenic reaction was stopped by immersing the slides in distilled water.

Following chromagenesis, the sections were counterstained with haematoxylin, dehydrated in an ascending series of ethanol solutions (90-99-100%), cleared in two changes of xylene and coverslipped under DePeX.

An assay control demonstrating cytokeratin immunoreactivity in colon mucosa was included to validate the ImmPress™ and chromagenic reagents. A 'no primary' control was included to assess non-specific binding of the secondary antibody and other assay reagents. Stained sections were analyzed, and suitable digital images were captured using an Olympus BX51 microscope with a Leica DFC290 camera.

Photographs of immunohistochemically stained cells are depicted in FIGS. 6A-6F and 7A-7H. Quantitation of the isoforms of the subunit can be accomplished as described herein. Following determination of the ratio of α3 isoform to α1 isoform content in the sample, a determination is made as to the likelihood of a therapeutic response to treatment with cardiac glycoside.

The term "about" is intended to mean±10%, ±5%, ±2.5% or ±1% relative to a specified value, i.e. "about" 22% means 22±2.2%, 22±1.1%, 22±0.55% or 22±0.22%.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A method of treating diseased tissue in a subject, said diseased tissue having a disease with an etiology associated with excessive cell proliferation, the method comprising:

obtaining a sample of the diseased tissue from the subject;

performing, on the sample, a Western Blot assay, an immunohistochemical staining assay, an enzyme linked immunoabsorbent assay, a Northern blot assay for measurement of mRNA to different Na,K-ATPase subunit isoforms on the sample of diseased tissue, a protein tissue assay or a cell lysate array assay to determine the content of α3 isoform and α1 isoform of the α-subunit of Na,K-ATPase present in the diseased tissue; and administering to the subject a composition comprising cardiac glycoside when the diseased tissue has a ratio of ≥0.3 for the α3 isoform, wherein the cardiac glycoside is selected from the group consisting of oleandrin, cinobufatalin, cinobufagin, resibufogenin, and bufalin.

2. The method of claim 1 further comprising:

providing a first primary antibody having a binding affinity for the α3 isoform;

a second primary antibody having a binding affinity for the α1 isoform; and conducting a radiometric or densitometric analysis of a gel.

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Generated by RT-PCR with mouse mammary tumor
      virus RT

<400> SEQUENCE: 1
cagctctgga gaactgctg                                                  19

<210> SEQ ID NO 2
<211> LENGTH: 20
<212> TYPE: DNA
<213> ORGANISM: Artificial Sequence
<220> FEATURE:
<223> OTHER INFORMATION: Generated with mouse mammary tumor virus RT

<400> SEQUENCE: 2
gtgtactcag tctccacaga                                                 20

<210> SEQ ID NO 3
<211> LENGTH: 10
<212> TYPE: DNA
<213> ORGANISM: Artificial Sequence
<220> FEATURE:
<223> OTHER INFORMATION: Non-specific primer set- forward; Misc featrue:
      n is a, c, g, or t; sequence is forward or revers
<220> FEATURE:
<221> NAME/KEY: misc_feature
<222> LOCATION: (1)..(10)
<223> OTHER INFORMATION: n is a, c, g, or t

<400> SEQUENCE: 3 nnnnnnnnnn                                                            10
```

3. The method of claim 1 further comprising:
immunochemically staining the α3 isoform and α1 isoform present in the sample of diseased tissue; and
measuring the content of the α3 isoform and the content of the α1 isoform in the sample.

4. The method of claim 1 further comprising:
indicating administration of the composition when the ratio of the α3 isoform to the α1 isoform ≥0.3.

5. The method of claim 1 further comprising: lysing or disrupting cells, tissues or biopsy samples; or fixing tissue sections for histopathologic examination from diseased in vivo cellular tissue to form the sample.

6. The method of claim 1, wherein the sample is cellular tissue, cellular mass, cellular lysate, membrane preparations prepared from these, or fixed histopathology slides thereof.

7. The method of claim 1, wherein the subject is a mammal.

8. The method of claim 1, wherein the ratio is of ≥0.5.

9. The method of claim 1, wherein the ratio is of ≥1.

10. The method of claim 1, wherein the ratio is of ≥10.

11. The method of claim 1, wherein the disease is selected from the group consisting of: 1) autoimmune diseases such as antigen-induced arthritis and allergic encephalomyelitis; 2) chronic inflammatory proliferative diseases such as rheumatoid arthritis, systemic-onset juvenile chronic arthritis, osteoporosis, and psoriasis; 3) proliferative diseases of the breast including fibrocystic disease; 4) proliferative diseases of the prostate including benign prostatic hyperplasia; 5) proliferative diseases of the eye including proliferative diabetic retinopathy; 6) vascular proliferative diseases including atherosclerosis and coronary stenosis; 7) cancer; and 8) tumor.

12. The method of claim 11, wherein the cancer or tumor is selected from the group consisting of colorectal cancer, head and neck cancer, adrenal cortical cancer, anal cancer, bile duct cancer, bladder cancer, bone cancer, bone metastasis, sarcomas of bone, brain cancer, breast cancer, cervical cancer, non-Hodgkin's lymphoma, rectal cancer, esophageal cancer, eye cancer, gallbladder cancer, gastrointestinal carcinoid tumor, gestational trophoblastic disease, Hodgkin's disease, Kaposi's sarcoma, kidney cancer, laryngeal and hypopharyngeal cancer, liver cancer, non-small cell lung cancer, small cell carcinomas, lung carcinoid tumors, malignant mesothelioma, metastatic cancer, multiple myeloma, myelodysplastic syndrome, nasal cavity and paranasal cancer, nasopharyngeal cancer, neuroblastoma, neoplasms of the central nervous system, oral cavity and oropharyngeal cancer, osteosarcoma, ovarian cancer, pancreatic cancer, penile cancer, pituitary cancer, prostate cancer, retinoblastoma, salivary gland cancer, sarcoma, skin cancer, stomach cancer, testicular cancer, thymus cancer, thyroid cancer, cancer of the ureter; uterine sarcoma, vaginal cancer, vulva cancer and Wilm's tumor.

13. The method of claim 11, wherein cancer is selected from the group consisting of prostate cancer, lung cancer, breast cancer, osteogenic sarcoma, osteogenic sarcoma, human brain cancer, glioblastoma multiforma and colon cancer.

14. The method of claim 1, wherein cardiac glycoside is present as part of an extract.

15. The method of claim 14, wherein the extract was prepared by supercritical fluid (SCF) extraction optionally in the presence of a modifier.

16. The method of claim 15, wherein the SCF extract further comprises at least one other pharmacologically active agent obtained during extraction.

17. The method of claim 14, wherein the SCF extract has been obtained from an oleander plant mass.

18. The method of claim 17, wherein the oleander plant mass comprises *Nerium* species or *Thevetia* species.

19. The method of claim 14, wherein the SCF extract has been obtained from toad skin or secretions derived therefrom.

20. The method of claim 1, wherein the cardiac glycoside is administered daily, every other day, every third day, every fourth day, semiweekly, weekly, biweekly, every three weeks, every four weeks, monthly, bimonthly, semimonthly, every three months, every four months, semiannually, annually, or according to a combination of any of the above.

21. The method of claim 1, wherein the cardiac glycoside is administered one or more times per day.

22. The method of claim 1, wherein the subject is administered a composition comprising 10 to 500 micrograms or 25 mg to 1000 mg of cardiac glycoside per day.

23. The method of claim 1, wherein the subject is administered 2 mg to 22.5 mg of cardiac glycoside per day.

24. The method of claim 1, wherein the subject is administered a supercritical fluid extract of a plant or animal source comprising 0.6 to 4.8 mg of cardiac glycoside.

25. A method of treating diseased tissue in a subject, said diseased tissue having a disease with an etiology associated with excessive cell proliferation, the method comprising:
indicating administration of the composition when the diseased tissue has a ratio of α3 isoform to α1 isoform of the α-subunit of Na, K-ATPase of ≥0.3; and
administering to the subject a composition comprising cardiac glycoside, wherein the cardiac glycoside is selected from the group consisting of oleandrin, cinobufatalin, cinobufagin, resibufogenin, and bufalin;
wherein the subject is a mammal.

26. The method of claim 25, further comprising:
obtaining a sample of the diseased tissue; and
measuring the ratio of the α3 isoform to the α1 isoform in the sample of diseased tissue.

27. The method of claim 26, wherein the ratio is of ≥1.

28. The method of claim 27, wherein the disease is selected from the group consisting of: 1) autoimmune diseases such as antigen-induced arthritis and allergic encephalomyelitis;
2) chronic inflammatory proliferative diseases such as rheumatoid arthritis, systemic-onset juvenile chronic arthritis, osteoporosis, and psoriasis; 3) proliferative diseases of the breast including fibrocystic disease; 4) proliferative diseases of the prostate including benign prostatic hyperplasia; 5) proliferative diseases of the eye including proliferative diabetic retinopathy; 6) vascular proliferative diseases including atherosclerosis and coronary stenosis; 7) cancer; and 8) tumor.

29. The method of claim 28, wherein the cancer or tumor is selected from the group consisting of colorectal cancer, head and neck cancer, adrenal cortical cancer, anal cancer, bile duct cancer, bladder cancer, bone cancer, bone metastasis, sarcomas of bone, brain cancer, breast cancer, cervical cancer, non-Hodgkin's lymphoma, rectal cancer, esophageal cancer, eye cancer, gallbladder cancer, gastrointestinal carcinoid tumor, gestational trophoblastic disease, Hodgkin's disease, Kaposi's sarcoma, kidney cancer, laryngeal and hypopharyngeal cancer, liver cancer, non-small cell lung cancer, small cell carcinomas, lung carcinoid tumors, malignant mesothelioma, metastatic cancer, multiple myeloma, myelodysplastic syndrome, nasal cavity and paranasal cancer, nasopharyngeal cancer, neuroblastoma, neoplasms of the central nervous system, oral cavity and oropharyngeal cancer, osteosarcoma, ovarian cancer, pancreatic cancer, penile cancer, pituitary cancer, prostate cancer, retinoblastoma, salivary gland cancer, sarcoma, skin cancer, stomach cancer, testicular cancer, thymus cancer, thyroid cancer, cancer of the ureter; uterine sarcoma, vaginal cancer, vulva cancer and Wilm's tumor.

* * * * *